United States Patent [19]

Hirayama et al.

[11] Patent Number: 4,747,059

[45] Date of Patent: May 24, 1988

[54] PROCESS AND APPARATUS FOR NAMING CHEMICAL STRUCTURES AND THE APPLICATION THEREOF

[75] Inventors: Kenzo Hirayama, Kanagawa; Tamano Taizo, Hyogo, both of Japan

[73] Assignee: Suntory Limited, Osaka, Japan

[21] Appl. No.: 809,514

[22] Filed: Dec. 16, 1985

Related U.S. Application Data

[63] Continuation-in-part of Ser. No. 681,688, Dec. 14, 1984, abandoned.

[51] Int. Cl.⁴ .......................... G06F 3/14; G06F 15/20
[52] U.S. Cl. ..................................... 364/496; 364/900
[58] Field of Search .................... 364/496, 200, 900

[56] References Cited

U.S. PATENT DOCUMENTS

| | | | |
|---|---|---|---|
| 4,085,443 | 4/1978 | Dubois et al. | 364/900 |
| 4,205,391 | 5/1980 | Ulyanov et al. | 364/900 |
| 4,473,890 | 9/1984 | Araki | 364/900 |

OTHER PUBLICATIONS

Rowlett, Jr. et al: a Computer-Based System for Handling Chemical Nomenclature and Structural Representations, Journal of Chemical Documentation, vol. 12, No. 2, 1972, pp. 125-128.
Fernelius W. C.: Present Status of Inorganic Chemical Nomenclature Journal Chemical Information Computer Science, vol. 21, No. 4, 1981, pp. 213-218.
Krishnamurthy E. V.: Wisenom, a Formal Organic Nomenclature System, Journal Chem. Inf. Sci., vol. 22, No. 3, 1982, pp. 152-160.
Barnard et al.: Computer Storage and Retrieval of Generic Structures in Chemical Patents, Journal Chem. Inf. Sci., vol. 22, No. 3, 1982, pp. 160-164.

*Primary Examiner*—Felix D. Gruber
*Attorney, Agent, or Firm*—Kenyon & Kenyon

[57] ABSTRACT

A novel method for naming chemical compounds comprises the steps of identifying a first component constituting the core of the compound according to predetermined first rules, naming the first component according to predetermined second rules, naming a secondary component of the first component according to predetermined third rules, modifying the name given for the first component by adding the name given for the second component to the name of the first component, and repeating the secondary-component naming and name-modifying steps for all of the secondary components in the compound. Such a method will give uniform rules for naming chemical compound, especially for organic compounds and for simply and easily naming new compounds.

26 Claims, 14 Drawing Sheets

FIG. 5-1(A)

TRI[3]ARENO-2(1)-AZADE (TYPE A)

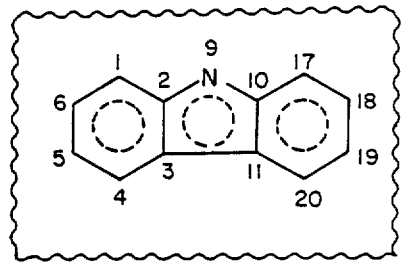

(TYPE B)

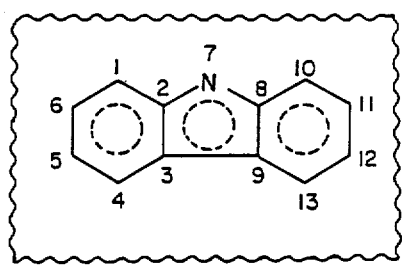

TRI[3]ARENO-2(I)-AZADE (TYPE A)

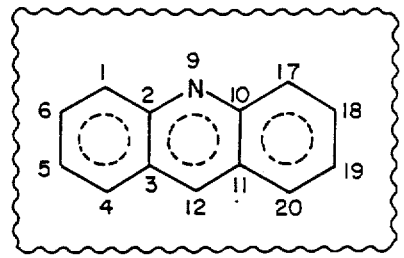

(TYPE B)

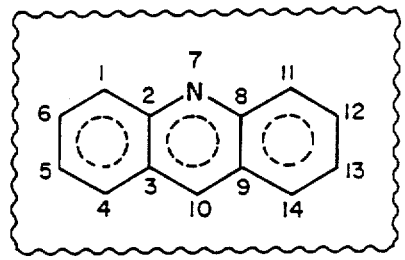

TRI[3]ARENO-2(4Z)-HOMO-2(1)-AZADE (TYPE A)

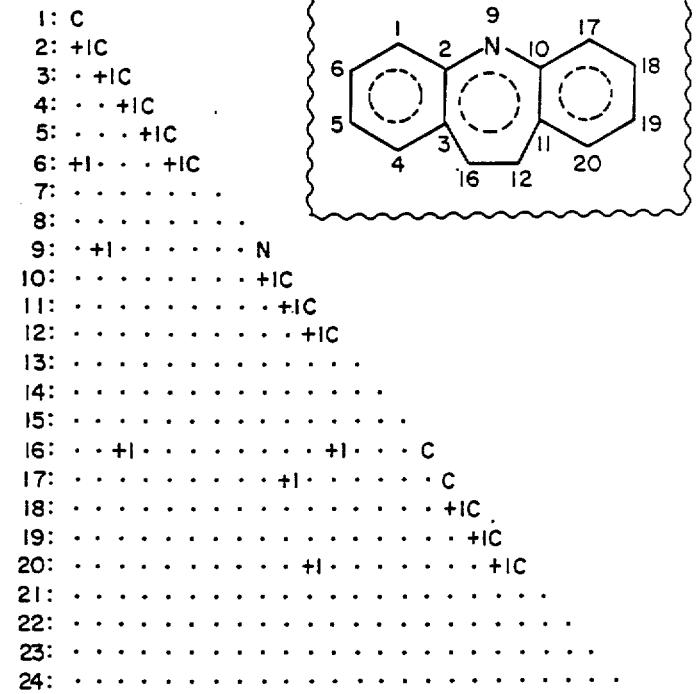

(TYPE B)

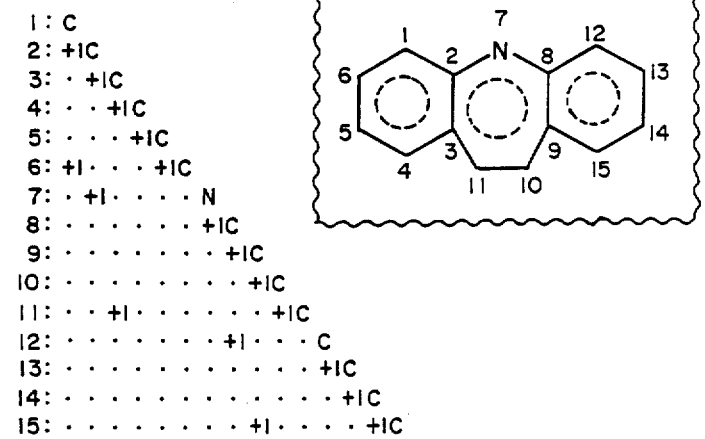

TRI[3]ARENO-2(4)-NOR-2(1)-AZADE (TYPE A)

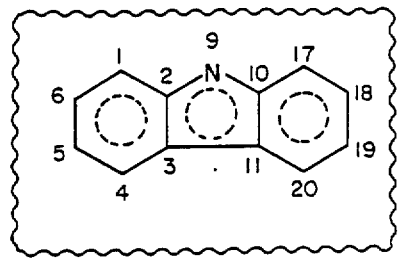

(TYPE B)

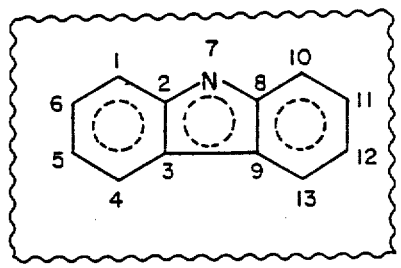

```
 1: C
 2: +1C
 3: · +1C
 4: · · +1C
 5: · · · +1C
 6: +1 · · · +1C
 7: · +1 · · · · N
 8: · · · · · · +1C
 9: · · +1 · · · · +1C
10: · · · · · · +1 · C
11: · · · · · · · · +1C
12: · · · · · · · · · +1C
13: · · · · · · · · +1 · · +1C
```

PENTA[5]CARBAN-3-EN-1-YNE

1: C
2: O3C
3: · O1C
4: · · O2C
5: · · · O1C

HEXA[6]CARBAN-3-EN-1-YNE

1: C
2: O3C
3: · O1C
4: · · O2C
5: · · · O1C
6: · · · · O1C

HEPTA[7]CARBAN-3-EN-1-YNE

1: C
2: O3C
3: · O1C
4: · · O2C
5: · · · O1C
6: · · · · O1C
7: · · · · · O1C

TRI[3]ARENO-2(4)-NOR-2(1)-AZA-2(1)-YL-4-PENTA[5]CARBAN-3-EN-1-YNE

```
 1: C
 2: +1C
 3: · +1C
 4: · · +1C
 5: · · · +1C
 6: +1 · · · +1C
 7: · +1 · · · · N
 8: · · · · · · +1C
 9: · · +1 · · · · +1C
10: · · · · · · · +1 · C
11: · · · · · · · · · · +1C
12: · · · · · · · · · · · +1C
13: · · · · · · · · +1 · · +1C
14:                       C
15:                      O3C
16:                      · O1C
17:              O1     · · O2C
18:                     · · · O1C
```

TRI[3]ARENO-2(4)-NOR-2(1)-AZADE

```
 1: C
 2: +1C
 3: · +1C
 4: · · +1C
 5: · · · +1C
 6: +1 · · · +1C
 7: · +1 · · · · N
 8: · · · · · · +1C
 9: · · +1 · · · · +1C
10: · · · · · · · +1 · C
11: · · · · · · · · · · +1C
12: · · · · · · · · · · · +1C
13: · · · · · · · · +1 · · +1C
```

DICYCLODODECA[10.(1:6)2]CARBANO-1-AZA-4-SULFADE

CYCLOOCTA[8][8(M)]ARENE

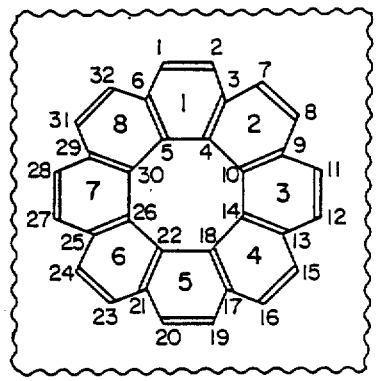

```
 1: C
 2: +1C
 3: · +1C
 4: · · +1C
 5: · · · +1C
 6: +1· · · +1C
 7: · · +1· · · C
 8: · · · · · · +1C
 9: · · · · · · · +1C
10: · · · +1· · · +1C
11: · · · · · · · +1· C
12: · · · · · · · · · +1C
13: · · · · · · · · · · +1C
14: · · · · · · · · +1· · +1C
15: · · · · · · · · · · · +1· C
16: · · · · · · · · · · · · +1C
17: · · · · · · · · · · · · · +1C
18: · · · · · · · · · · · · +1· · +1C
19: · · · · · · · · · · · · · · +1· C
20: · · · · · · · · · · · · · · · +1C
21: · · · · · · · · · · · · · · · · +1C
22: · · · · · · · · · · · · · · · +1· · +1C
23: · · · · · · · · · · · · · · · · · +1· C
24: · · · · · · · · · · · · · · · · · · +1C
25: · · · · · · · · · · · · · · · · · · · +1C
26: · · · · · · · · · · · · · · · · · · +1· · +1C
27: · · · · · · · · · · · · · · · · · · · · +1· C
28: · · · · · · · · · · · · · · · · · · · · · +1C
29: · · · · · · · · · · · · · · · · · · · · · · +1C
30: · · · · +1· · · · · · · · · · · · · · · · +1· · +1C
31: · · · · · · · · · · · · · · · · · · · · · · · · +1· C
32: · · · · · +1· · · · · · · · · · · · · · · · · · · · +1C
```

TETRA [2.(1:1:A)2] ARENO-PERHYDRO-1(5):3(2):1(3):4(2):2(3)-QUINIYL-1,2,3,4,5--PENTA[5]CARBANE

```
 1: C
 2: OlC
 3: · OlC
 4: · · OlC
 5: · · · OlC
 6: Ol · · · OlC
 7: · Ol · · · · C
 8: · · · · · · OlC
 9: · · · · · · · OlC
10: · · Ol · · · · · OlC
11: · · · · · · · · · · C
12: Ol · · · · · · · · OlC
13: · · · · Ol · · · · · · C
14: · · · · · · · · · Ol · OlC
15: · · · · · · · · · · Ol · · C
16: · · · · · Ol · · · · · · · OlC
17:        Ol                    C
18:              Ol          OlC.
19:    Ol                   .· OlC
20:                    Ol · · OlC
21:           Ol              · · · OlC
```

TRIDECA [7.(2)1.(4)3.(5)2] CARBAN-3-ENO-1-YL-1-[1]OXANE-10-(YL-1-[1]AZANO-1-YL-1-[1]CARBANE)-7-(YL-1-[1]AZANO-1-YLIDEN-2-TETRA[4]CARBANO-1-YL-1-[1]OXANE)-8-((YLIDEN-2-DI[2]AZANO-1-YL-1-[1]CARBANO-1-YL-1-[1]AZANE-1-YLIDEN-1-[1]SULFANE)-8-YL-1-[1]OXANO-1-YL-1-[1]CARBANE)-13-YL-1-[1]SULFANO-1-YL-1-[1]AZANO-1-YL-1-[1]CARBANE

PROCESS AND APPARATUS FOR NAMING CHEMICAL STRUCTURES AND THE APPLICATION THEREOF

CROSS-REFERENCE TO THE CO-PENDING APPLICATION

The present application is a Continuation-in-Part application of U.S. patent application Ser. No. 681,688, filed Dec. 14, 1984, and now abandoned, by Kenzo Hirayama et al and assigned to the common assignee.

BACKGROUND OF INVENTION

The present invention relates generally to the nomenclature of organic chemical compounds and their structures. More specifically, the invention relates to a novel process and system for naming chemical compounds, which allows linear notation of chemical structure in an extremely simple way. Hereinafter, the system of the chemical nomenclature according to the present invention will be called "Radial Nomenclature".

This invention is a discovery of a consistent rule that applies to all organic compounds for the linear notation of chemical structures. The invention incorporates specific methods suitable for visual and aural information exchange between humans as well as specific methods for information processing by computers, and is a linear notation of chemical structures using natural language that is extremely simple, being composed of approximately a hundred basic terms and a systematic grammar. The inventor names this notation "Radial Nomenclature", which expresses the characteristics of this notation.

It is now 200 years since the molecular structure of organic compounds began to be researched, but as organic compounds since then have been independently named without a unifying logic, there has been confusion in science and industry.

In order to resolve this problem, a movement began to establish means based on molecular structures, and in AD 1892, the first international proposal (the so-called "Geneva Rules") was made. However, as this proposal could be applied only to a portion of organic compounds, this was revised and extended by the Commission for the Reform of Nomenclature in Organic Chemistry of the International Union of Chemistry (I.U.C.), and this work was succeeded by the Commission of Nomenclature of Organic Chemistry of the International Union of Pure and Applied Chemistry (I.U.P.A.C.).

This commission continues its work to complete the establishment of a set of IUPAC NOMENCLATURE RULES, but as compounds of new types appear, the rules are revised and supplemented in extensive detail, so that a consistency in the rules is becoming scarce, and the corpus has become a rule book of over several hundred basic terms and over 300 pages. As a result, this nomenclature has become a useful tool for nomenclature specialists, but a grammatically difficult "Basque tongue" for students new to chemistry.

On the one hand, information on over 6 million organic compounds are now extensively used in chemical industry and research, but notwithstanding the development of computers as tools for information processing, as there is no consistent nomenclature, serial numbers that are unrelated to chemical structures are used in order to relate chemical structures to compound names in computer processing.

On the other hand, we have the Wiswesser Line-Formula Chemical Notation (usually abbreviated as WLN) and Nodal Nomenclature (Noel Lozach, Angew. Chem. Int. Ed. Engl. 18, 887–899 (1979); 23, 33–46 (1984)) which are linear notations or nomenclature of chemical structures that are logically consistent.

In terms of the unequivocal correspondence between notations or names and chemical structures, the former is said to be good, and it is assumed that the latter also corresponds.

WLN is a predominantly character-and-symbol based linear notation that is suitable for information processing using computers, but as it is not in natural language, it lacks straightforwardness for human senses.

The reason that the latter Nodal Nomenclature was assumed to have unequivocal correspondence between names and structures is that in that system, the smallest component of the skeletal structures of compounds as identified as the atom, and their mutual relationship is notated linearly, so that it has similarities to this invention, but its applicability to all compounds has still not been demonstrated.

SUMMARY OF THE INVENTION

Therefore, it is a principal object of the present invention to provide a novel process for naming chemical structure of organic compounds in a simple and unambiguous way.

Another object of the present invention is to provide a novel notation process for the chemical structure which is applicable to all chemical structures, and especially to organic compounds.

A further object of the present invention is to provide a system for performing the novel notation process according to the invention.

In order to accomplish the aforementioned and other objects, a notation process for chemical compounds according to the present invention is based on the following principles:

1. The chemical structure of all organic compounds are (I) considered to be acyclic hydrocarbons; (II) considered to be alicyclic hydrocarbon compounds; (III) considered to be aromatics excepting those in item IV; and/or (IV) cyclic fused aromatic rings, each of groups (I) through (IV) having corresponding noncarbon isohydrides.

2. (I) and (II) are shown with the relationship between skeletal atoms, and (III) and (V) are shown with the relationship between aromatic rings in a logically consistent manner.

3. Even when the above components are mutually bonded to form a different type of organic compound, the original name and numbering of skeletal atoms used in the nomenclature of the original constitutional elements are retained as unique characteristics of that element.

4. The names of all compounds begin with the expression of the core, following the notation that has been formulated, and the names of the substituent portions are added in turn.

5. As a logically unified method was established for expressing the mutual relationship of bonding of the consitutional elements, this supports the mechanical interconversion of names and chemical structures of the formula notation.

6. As the terms based on natural language are used in the formula notation, the notation is suitable for human vision and hearing too.

According to one aspect of the invention, a method for naming chemical compounds comprises the steps of:

identifying a first component constituting the core of the compound according to predetermined first rules;

naming the first component according to predetermined second rules;

naming a secondary component of the first component according to predetermined third rules;

modifying the name given for the first component by adding the name given for the second component to the name of the first component; and repeating the secondary-component naming and name-modifying steps for all of the secondary components in the compound.

The chemical compound is an organic compound. The first component is classified from among a first group consisting of acyclic hydrocarbons, a second group consisting of alicyclic hydrocarbon compounds, a third group consisting of aromatics excepting those classified in a fourth group, and the fourth group consisting of cyclic fused aromatic rings, each group having corresponding noncarbon isohydrides. The first component to be classified in the first and second groups are skeletal atoms. On the other hand, the first component to be classified in the third and fourth groups are aromatic rings.

The original name and numbering of the skeletal atoms used in nomenclature of the original constitutional element are retained as unique characteristics of the element even when the components are mutually bonded to form a different type of organic compound. All the names given to the chemical compounds begin with the name of the first component. The names given to the second components follow the name of the first component.

In the preferred method, natural language are used in the formula notation.

According to another aspect of the invention, a system for naming chemical compounds comprises storage means for storing name stems and rules for naming compounds, input means for inputting data concerning chemical compounds, processing means for accepting data from the input means, retrieving name stems and rules from the storage means and manipulating data accepted from the input means according to the rules stored in the storage means, and output means for displaying the results of manipulations performed by the processing means.

The input means is adapted to accept data in the form of the chemical formula of the compound to be named. The output means is associated with the input means for displaying input data. The output means incorporates a graphic display, and the input means allows graphic input. The storage means stores the name stems in the form of a table.

BRIEF DESCRIPTION OF THE DRAWINGS

The present invention will be understood more fully from the detailed description given herebelow and from the accompanying drawings of the preferred embodiment of the invention, which, however, should not be taken to limit the invention to the specific embodiment but are for explanation and understanding only.

In the drawings:

FIGS. 5-1(A) to 5-5((I) are examples of names according to the invention and the corresponding chemical formula.

DETAILED DESCRIPTION OF THE INVENTION

Figure 1:
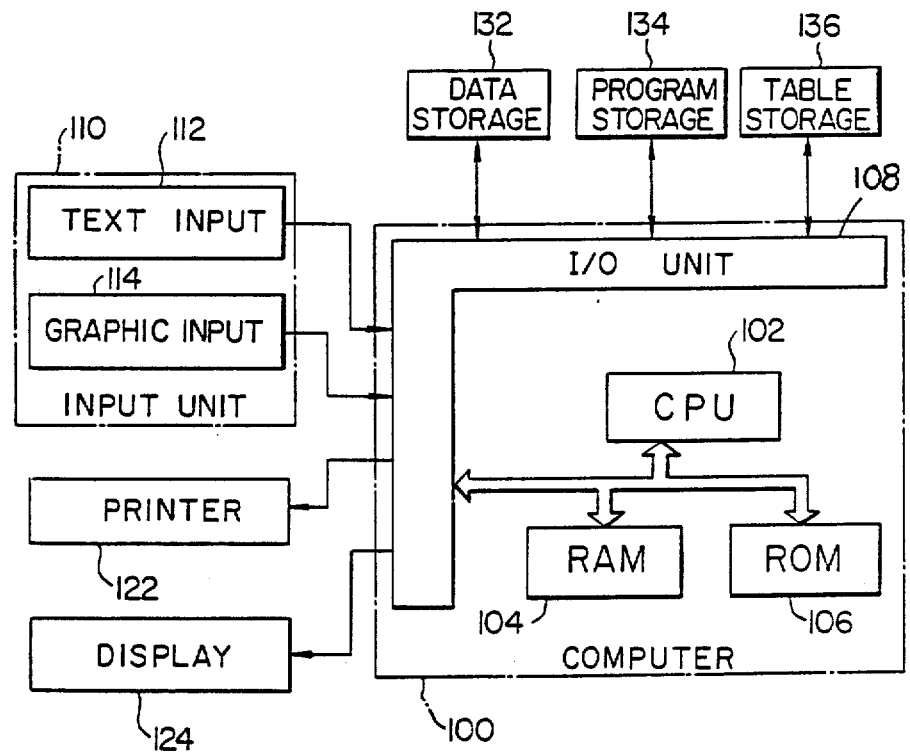
FIG. 1 is a schematic block diagram of the preferred embodiment of a naming system in accordance with the present invention.

Hereafter disclosed is the preferred embodiment of a notation process for chemical compounds, especially organic compounds, according to the invention and a system for implementing the preferred embodiment of the notation process.

Before disclosing the preferred embodiment of the naming system according to the invention, the fundamental principles of notation for chemical compounds according to the present invention will be described to facilitate better understanding of the present invention.

1. Decomposing Chemical Structures into Their Components

A chemical structure is decomposed into its components as follows:

(1) All atoms other than hydrogen are regarded as skeletal atoms.

(2) The skeletal structure is decomposed into its components as stated below, and when there is a choice for how the structure is to be decomposed, then that one is chosen which gives the least number of components.

(3) Moniliform cyclic structures, which are formed by four- to eight-membered rings whose two adjacent rings have only two atoms in common, are isolated as Group IV.

(4) Honeycomb-like fused systems of six-membered rings and their modified systems with up to four- or eight-membered expanded or contracted peripheral rings with maximum number or non-adjacent double bonds are isolated as Group III from what remains after process (3).

(5) Cyclic parts are isolated as Group II from what remains after process (4).

(6) Every continuation of identical atoms in what remains after process (5) are isolated as Group I.

These components in four Groups are classified into fundamental skeletons and their modifications as follows:

a. The skeletons of Group III and IV, which are composed of only six-membered rings with identical atoms and with the maximum number of non-adjacent double bonds are the fundamental skeletons, while the other components of these Groups are modifications of the fundamental skeletons.

b. The skeletons of Group II, which are composed of one kind of atom linked to each other by single bonds are the fundamental skeletons, while the other components of this Group are modifications of the fundamental skeletons.

c. The skeletons of Group I, which are composed of single bonds alone are the fundamental skeletons, while the other components of Group I are modifications of the fundamental skeletons.

2. Naming Components

Each component obtained by the preceding process is named as follows:

(Name of a Component)  (1)

= (Name of the Fundamental Skeleton)

$$+ \sum_{g=1}^{h} \text{(Notation for Modification)}_g$$

The formula $$\sum_{g=1}^{h}$$

stands for citing the 1st variable, 2nd variable, and so on up to the h-th, one by one in this order, and the formula A+B+ ... stands for citing the terms A, B, ... in this order.

(1) The Names of Fundamental Skeletons

The name of each fundamental skeleton is made by citing the variables in the following formula according to Table 1.

(Name of the Fundamental Skeleton) =  (2)

$$A + B + C + \left[\sum_{a=1}^{b} D_a\right] + \left[\sum_{c=1}^{d} E_c\right] + F + G + H$$

TABLE 1

| Variables | Applicable Groups | Meanings | Cipher or Term for Each Variable |
|---|---|---|---|
| A | II and IV | The number of cycles | Multiplicative 1st Series*1 |
| B | II AND IV | Existence of nodal cycles | The term CYCLO |
| C | I to IV | The number of nodes | Multiplicative 1st Series*1 |
| D | I, II and IV | Size of cycle and unbranched chains, and location of branching points | The number of nodes and locants of branching points |
| E | III | Length, location, and stretching direction of ring-lines | The locant, direction cipher and the number of rings |
|   | IV | Fusing site of rings | The direction cipher |
| F | I and II | Kinds of atoms | The terms *2 |
|   | III and IV | Kinds of atoms | The terms *2; CARB is omitted |
| G | I and II | Skeleton composed of atoms | The term AN |
|   | III and IV | Skeleton composed of rings | The term AREN |
| H | I to IV | Without modification and substitution | The term E |
|   |   | With modification and/or substitution | No term before EN and YN The term O before others |

*1 The variables A and C are multiplicatives of the first series as follows:

| 2 di | 11 undeca | 21 henicosa | 31 hentriaconta |
|---|---|---|---|
| 2 di | 12 dodeca | 22 docosa | 32 dotriaconta |
| 3 tri | 13 trideca | 23 tricosa | 33 tritriaconta |

TABLE 1-continued

| 4 tetra | 14 tetradeca | 24 tetracosa | . . |
| 5 penta | 15 pentadeca | 25 pentacosa | . . |
| 6 hexa | 16 hexadeca | 26 hexacosa | . . |
| 7 hepta | 17 heptadeca | 27 heptacosa | 40 tetraconta |
| 8 octa | 18 octadeca | 28 octacosa | 50 pnetaconta |
| 9 nona | 19 nonadeca | 29 nonacosa | 60 hexaconta |
| 10 deca | 20 icosa | 30 triaconta | 70 heptaconta |
|   |   |   | 80 octaconta |
|   |   |   | 90 nonaconta |
| 100 hecta | 400 tetracta | 700 heptacta | 1000 kilia |
| 200 dicta | 500 pentacta | 800 octacta | 2000 dilia |
| 300 tricta | 600 hexacta | 900 nonacta | 3000 trilia |

*2 Terms denoting elements are: C = carb, Si = Sil, Ge = germ, Sn = stann, Pb = plumb, B = bor, N = az, P = phosph, As = ars, Sb = stib, Bi = bismuth, Hg = mercur, O = ox, S = sulf, Se = sel, Te = tell, Po = pol, F = flour, Cl = chlor, Br = brom, I = iod, At = astst.

(2) The Modification of Fundamental Skeletons

Modification has the following functions:
a. change of bonding stage between skeletal atoms.
b. Addition or deletion of skeletal atoms.
c. Partial exchange of skeletal atoms with atoms of other kinds of elements Modification of a fundamental skeleton is described by citing the variables in the next formula according to Table 2.

$$\text{(Notation for Modification)} = \sum_{g=1}^{h} \left( \sum_{i=1}^{j} I_i + J + K + L \right)_g \quad (3)$$

TABLE 2

| Variables | Applicable Groups | Meanings | Cipher or Term for Each Variable | |
|---|---|---|---|---|
| I | I to IV | Modified position of the fundamental skeleton | Locants in the fundamental skeleton | |
| J | I to IV | The number of identical modifications | Multiplicative 1st series*1 | |
| K |   | Kinds of modifications |   |   |
|   | I, II | Change of a single bond to a double bond | The term EN | — |
|   | I, II | Change of a single bond to a triple bond | The term YN | — |
|   | III | Hydrogenative deletion of an atom of an internal ring | — | The term DELE |
|   | III | Hydrogenative deletion of a bond of an internal ring | — | The term SEC |
|   | III, IV | Insertion of an atom in a periferical bond | — | The tern HOM |
|   | III, IV | Deletion of a non-angular periferical atom | — | The term NOR |
|   | III, IV | Linking two ring atoms | — | The term CYCL |
|   | III, IV | Change of a double bond to a triple bond | — | The term DEHYDR |
|   | III, IV | Change of a double bond to a single bond | — | The term HYDR |
|   | III, IV | Exchange of a skeletal atom by another kind of atom | — | The term for element *2 |
| L | I to IV | Without more modifications or | The term E | The term ADE |

TABLE 2-continued

| Variables | Applicable Groups | Meanings | Cipher or Term for Each Variable |
|---|---|---|---|
| | | substitutions With further modification and/or substitutions | No term after NOR The term A after the terms for elements The term O after other terms |

3. Choice of the Core among the Components

The core is chosen among the components by applying the following criteria in the described order until the decision is made. The choice goes to the component
 a. whose Group number is the largest;
 b. whose variable A denoted by a multiplicative is the largest;
 c. whose variable C denoted by a multiplicative is the largest;
 d. whose series of variables $$\left[\sum_{a=1}^{b} D_a\right]$$

is prior;
 e. whose series of variable $$\left[\sum_{c=1}^{d} E_c\right]$$

is prior;
The priority of the series $$\left[\sum_{a=1}^{b} D_a\right] \text{or} \left[\sum_{c=1}^{d} E_c\right]$$

is defined as in the following.
When the series $$\left[\sum_{a=1}^{b} D_a\right] \text{or} \left[\sum_{b=1}^{d} E_c\right]$$

is compared variable to variable, that one is prior which contains the prior variable prescribed by the following criteria on the occasion of the first difference.
 a. The larger number denoting size, or length is prior.
 b. The smaller locant is prior.
 c. That cipher denoting direction is prior which precedes in alphabetical order.
 d. A variable is prior to a variable which constitutes the first part of the former variable.

4. Composition of Names of Compounds

Components other than the core are all substituting components. The bonding relations among the core and the substituting components are as in the following example:

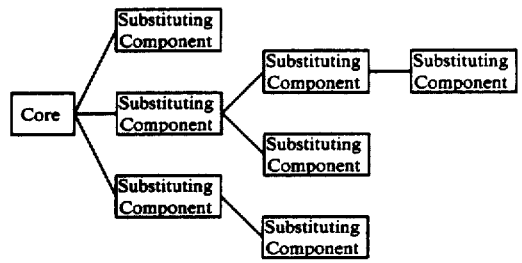

A compound is named by citing first the core, then the substituting components one by one from the one attached to the core to the terminal one of every branch, processing in alphabetical order of the name at each branching point.

(Name of a Compound)      (4)

$$= \text{(Name of the Core)} + \sum_{u=1}^{y} \text{(Name of the Substituting Component)}_u$$

The core is the component preceding those substituting components which are attached to it. A substituting component can also be the preceding component of other substituting components which attach to it and are not located between it and the core. A substituting component is the subsidiary substituting components of their preceding substituting components.

The name of the core is designated by the name of the component.

5. Naming Substituting Components

Each substituting component is named by citing the variables in the next formula according to Table 3.

(Name of a Substituting Component)      (5)

$$= \text{(Conjunction)} + \text{(Name of the Component)}$$

$$= \sum_{m=1}^{n} a_m + \beta + \sum_{q=1}^{r} (\gamma + \delta)_q + \sum_{s=1}^{t} \epsilon_s$$

$$+ \text{(Name of the Component)}$$

TABLE 3

| Variables | Meanings | Cipher or Term for Each Variable |
|---|---|---|
| α | Points in the preceding component to which the substituting component is bonded | The locant in the preceding component |
| β | The number of identical substituting components | Multiplicative 1st series*1 |
| γ | The number of identical bonds between the substituting component and the preceding component | Multiplicative 2nd series*3 |
| δ | Kinds of bonds with which the substituting component is bonded with the preceding component: | |
| | a. Single valence bond | The term YL |
| | b. Double valence bond | The term YLIDEN |
| | c. Triple valence bond | The term YLIDYN |
| ε | Points in the substituting component from which the valence bonds stretch out | The locant in the substituting component |

TABLE 3-continued to the preceding component

*3 The following is the list of the multiplicatives of
the second series.

| | | | |
|---|---|---|---|
| 2 bi | 8 octoni | 14 quaterdeni | 20 viceni |
| 3 ter | 9 noveni | 15 quideni | 21 unviceni |
| 4 quater | 10 deni | 16 sedeni | 30 terceni |
| 5 quini | 11 undeni | 17 septedeni | 40 quaterceni |
| 6 seni | 12 duodeni | 18 octodeni | 50 quiceni |
| 7 septeni | 13 terdeni | 19 novedeni | 60 seceni |

6. Naming Monoatomic Substituting Components

Monoatomic fundamental skeletons can be denoted by the variable F out of variables A to L, because they are composed of one skeletal atom and cannot be modified. Thus, that substituting component with subsidiary substituents which are derived from a monoatomic fundamental skeleton is denoted by formula (5) with variable F instead of $$\sum_{s=1}^{l} \epsilon_s + \text{(Name of the Component), i.e.,}$$

$$\text{(Name of a Monoatomic Substituting Component with Substituents)} = \sum_{m=1}^{n} a_m + \beta + \sum_{q=1}^{r} (\gamma + \delta)_q + F \quad (6)$$

In the case of unsubstituted substituents derived from monoatomic fundamental skeletons, substituting components are named by citing the variables in the next formula according to the Tables 3 and 4.

$$\text{(Name of a Monoatomic Substituting Component without Substituents)} = \sum_{m=1}^{n} a_m + \beta + F + \sum_{q=1}^{r} (\gamma + \delta')_q \quad (7)$$

TABLE 4

| Variables | Meanings | Term for Each Variable |
|---|---|---|
| δ' | Kinds of bonds with which the substituting component is bonded with the preceding component: | |
| | a. Single valence bond | The term ANT |
| | b. Double valence bond | The term ENT |
| | c. Triple valence bond | The term INT |

7. Complex Variables

Variables D, E, I, α, and ε, which are not defined in detail earlier, are composed of elemental variables as follows:

(1) Elemental Variables

Elemental variables R and S denote locants of nodes, i.e., of skeletal atoms or rings, and T denotes locants of atoms in the nodal ring.

Elemental variable U denotes the locant of the originating nodal ring in the case of Group III as shown below:

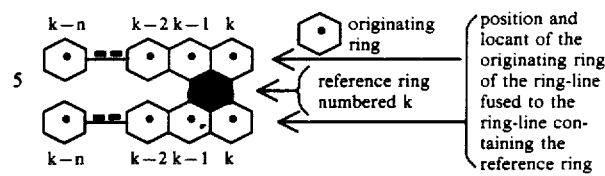

The originating ring is the ring at which the numbering of rings in the ring-line begins, and is defined as the left-end ring of a lateral ring-line, or the ring of an oblique ring-line nearest to the main ring-line.

The reference ring which determines the locant and the direction cipher of a ring-line is (i) that previously numbered ring of the oblique ring-line, or (ii) the left-end ring of that previously numbered lateral ring-line, to which the said ring-line is fused.

When skeletal nodes are hexagonal rings, there are more than one fusing cite of nodes, which are denoted by the variable V. In the case of Group III, the sprouting directions of the ring-line are defined A, B, C, D, E, F, G, and H as shown below, and in the case of Group IV, the fusing cite of nodes in a monoliform cycle is defined as M, P, and V as shown below.

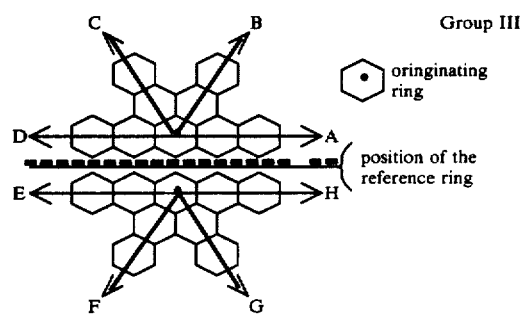

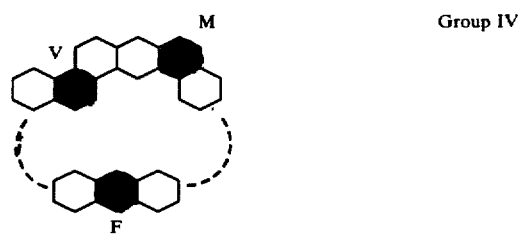

Elemental variable W denotes the number of nodes, i.e. of skeletal atoms or rings.

(2) Variable D—(a) Size and Locants of Unbranched Chains.

In the case of Group I, the length and locant of an unbranched chain of nodes are denoted by the variable D. This variable is composed of two elemental veriables R and W as $$D_a = {}^{R_a}W_a$$

where $W_a$ indicates the number of nodes of the a-th chain, while $R_a$ indicates the locant of the node, from which the a-th chain sprouts out. Locants are defined as follows First, the longest unbranched chain in the fundamental skeleton is defined as the main chain, and its nodes are consecutively given locants from 1 beginning at one end so as to give the lowest series of locants of the branching nodes.

Next, the nodes of branches sprouting out from the main chain are given locants consecutively following the locants of the main chain, branch by branch in the increasing order of their locants, i.e., the locants of the nodes in the main chain from which the branches sprout out.

The example shows the numbering of the nodes and matrix of the variable $D_a$. The elemental variable $R_1$ is always omitted, because the main chain is not branched out from another chain.

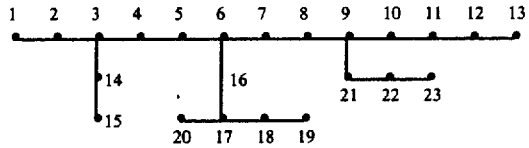

| a | $R_a$ | $W_a$ |
|---|-------|-------|
| 1 | —     | 13    |
| 2 | 3     | 2     |
| 3 | 6     | 4     |
| 4 | 17    | 1     |
| 5 | 9     | 3     |

Therefore, the series of $D_a$ is $$\left[\sum_{a=1}^{5} D_a\right] = [13^3 2^6 4^{17} 1^9 3]$$

(3) Variable D—(b) Size and Locants of Cycles and Bridges.

In the cases of Groups III and IV, the size and locants of a cycle or a bridge of nodes are denoted by the variable D. This variable is composed of three elemental variables as $$D_a = {}^{Ra:Sa}W_a$$

where $W_a$ indicates the number of nodes of the a-th unbranched chain composing a cycle or a bridge, and $R_a$ and $S_a$ indicate locants of the nodes to which both end-nodes of the a-th chain are bound. Locants are defined as follows.

First, the nodes of the largest cycle (called the main cycle) are consecutively given locants from 1 so as to give the lowest series of locants of the bridgehead nodes (the nodes branching out bridges).

Next, the nodes of bridges (unbranched or branched) are consecutively given locants one by one following the node locants of the main cycle, in the increasing order of the series of locants of the bridgehead nodes (if there are more than two locants, the series of the two lowest locants) of bridges. Nodes of each unbranched chain are given locants from the end bound to the lower numbered node.

The examples show the numbering of nodes and the matrix of the variables $D_a$. As the elemental variable $R_1$ is always 1, and $S_1 = W_1$, $R_1$ and $S_1$ are omitted in the series of variable $D_1$.

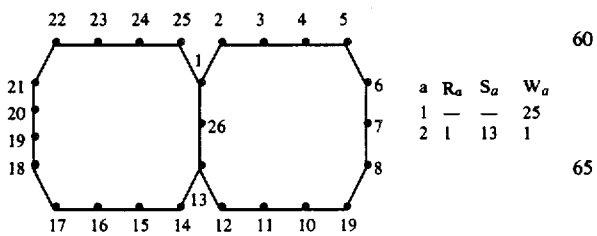

| a | $R_a$ | $S_a$ | $W_a$ |
|---|-------|-------|-------|
| 1 | —     | —     | 25    |
| 2 | 1     | 13    | 1     |

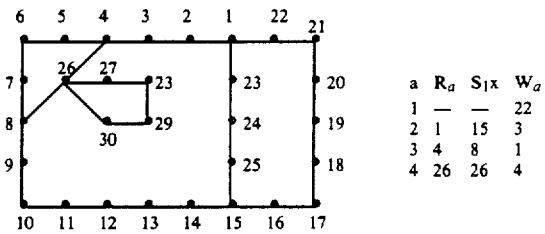

| a | $R_a$ | $S_1x$ | $W_a$ |
|---|-------|--------|-------|
| 1 | —     | —      | 22    |
| 2 | 1     | 15     | 3     |
| 3 | 4     | 8      | 1     |
| 4 | 26    | 26     | 4     |

Therefore, the series of the variables $D_a$ of the examples are $$\left[\sum_{a=1}^{2} D_a\right] = [25^{1:13}1], \text{ and } \left[\sum_{a=1}^{4} D_a\right] = [22^{1:15}3^{4:8}1^{26:26}4],$$

respectively.

(4) Variable E—(a) The Case of Group III

Ring-lines of Group III are denoted by the variable E, which is composed of three elemental variables U, V, and W as $$E_e = {}^{Ue + Ve}W_e$$

where $W_e$, $U_e$, and $V_e$ indicate the number of rings in the e-th ring-line, the locant of the originating ring of the e-th ring-line, and the sprouting direction of the e-th ring-line, respectively.

Rings of ring-line are numbered as follows:

First, the longest ring-line in the fundamental skeleton is defined as the main ring-line, and its rings are consecutively numbered from 1 beginning at one end so as to give the prior series of the variables $U+V$ of ring-lines fusing to the main ring-line.

Next, rings of each ring cluster fusing to the main ring-line are consecutively numbered cluster by cluster following the ring-numbers of the main ring-line, in the prior order of $U+V$.

The example shows the numbering of ring-nodes and the matrix of the variable $E_e$. The elemental variables $U_1$ and $V_1$ are always omitted, because the main ring-line has no previously numbered ring-line, and the direction cipher of the main ring-line is always A.

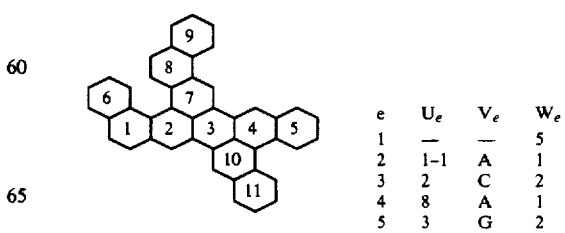

| e | $U_e$ | $V_e$ | $W_e$ |
|---|-------|-------|-------|
| 1 | —     | —     | 5     |
| 2 | 1-1   | A     | 1     |
| 3 | 2     | C     | 2     |
| 4 | 8     | A     | 1     |
| 5 | 3     | G     | 2     |

Therefore, the series of $[E_e]$ is $$\left[\sum_{e=1}^{5} E_e\right] = [5^{1-1}A_1{}^2C_2{}^{8}A_1{}^{3}G_2]$$

(5) Variable E—(b) The Case of Group IV.

The fusing site of the rings of Group IV is denoted by the variable E, which is indicated by the elemental variable V as $$E_e = V_e$$

The series of variable $V_e$ is described in the order or ring-numbers defined in section 7(3) variable D. The ring-numbers of the following two examples correspond to the node-numbers of the first example in 7(3).

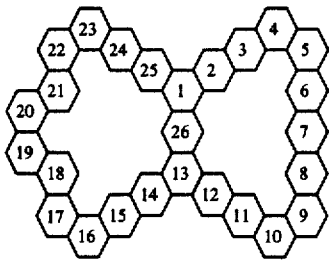

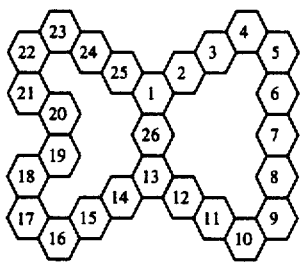

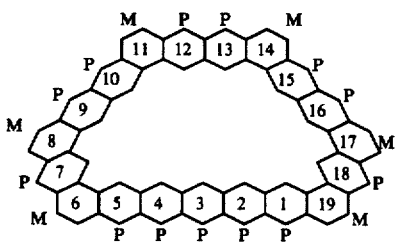

Therefore, the series of variables $$\left[\sum_{e=1}^{2} E_e\right]$$

of these examples are

[VPPMMPPPMMPPVPPMMVMMVMMPP.P]

and

[VPPMMPPPMMPPVPPMMMVVMMMPP.P], respectively. Variables $E_e$ are separated by each other with a period. These ciphers are rewritten by using Arabic numerals to indicate the number of times of the identical ciphers are repeated.

$$[1V_2{}^{PM}3P_2{}^{MP}1V_2{}^{PM}1V_2M_1V_2{}^{MP}.1P]$$

and $$[1V_2{}^{PM}3P_2{}^{MP}1V_2P_3M_2V_3M_2P.1P],$$

respectively.

The variable E for a monocycle is cited as prior as possible. The third example is denoted as $$[5P_1{}^{MPM}2P_1M_2P_1M_2P_1{}^{MPM}]$$

(6) Variables I, α, and ε

These variables denote locants, and locants of modification are denoted by the variable I.

When the modification is bipedal, cited by EN, YN, SEC, CYCL, or DEHYDR, the variable I is indicated by two elemental variables, as $$I = R:S$$

and locants for point modification, DELE, HOM, NOR, HYDR, or HETER citing the replacement of skeletal atoms by hetero atoms, are indicated by an elemental variable, as $$I = R$$

In the series of variable $$\sum_{k=1}^{l} I_k$$

for identical modifications, I's are separated with a comma from each other.

The following examples show locants of modification EN, and HETER modification, respectively.

III

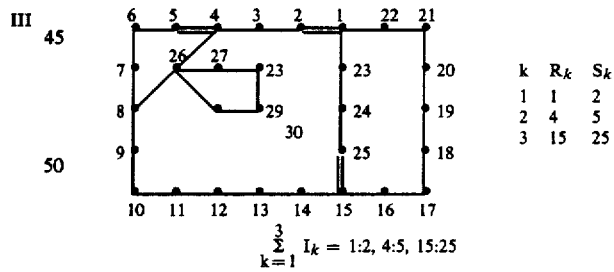

$$\sum_{k=1}^{3} I_k = 1:2,\ 4:5,\ 15:25$$

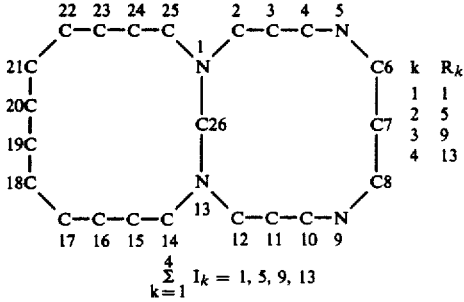

$$\sum_{k=1}^{4} I_k = 1,\ 5,\ 9,\ 13$$

Variables α and ε denoting locants of free valence bonds are indicated similarly to I.

8. GENERAL STRUCTURE OF COMPUTERIZED SYSTEM FOR NOTATION

In order to implement the aforementioned notation process for chemical compounds, the preferred computer system comprises a computer 100, an input unit 110, a printer 122 and/or a display 124, and external storage such as data storage 132 for storing names and corresponding chemical formulae as previously named, program storage 134 and table storage 136, as shown in FIG. 1. As is well known, the computer 100 includes an input/output (I/O) unit 108, a central processing unit (CPU) 102, a random-access memory (RAM) 104 and a read-only-memory (ROM) 106. The input unit 110 comprises a graphic input unit 112 for performing data input in the form of chemical formulae and a text input unit 114 for performing data input in the form of alphanumeric characters.

Figure 2:
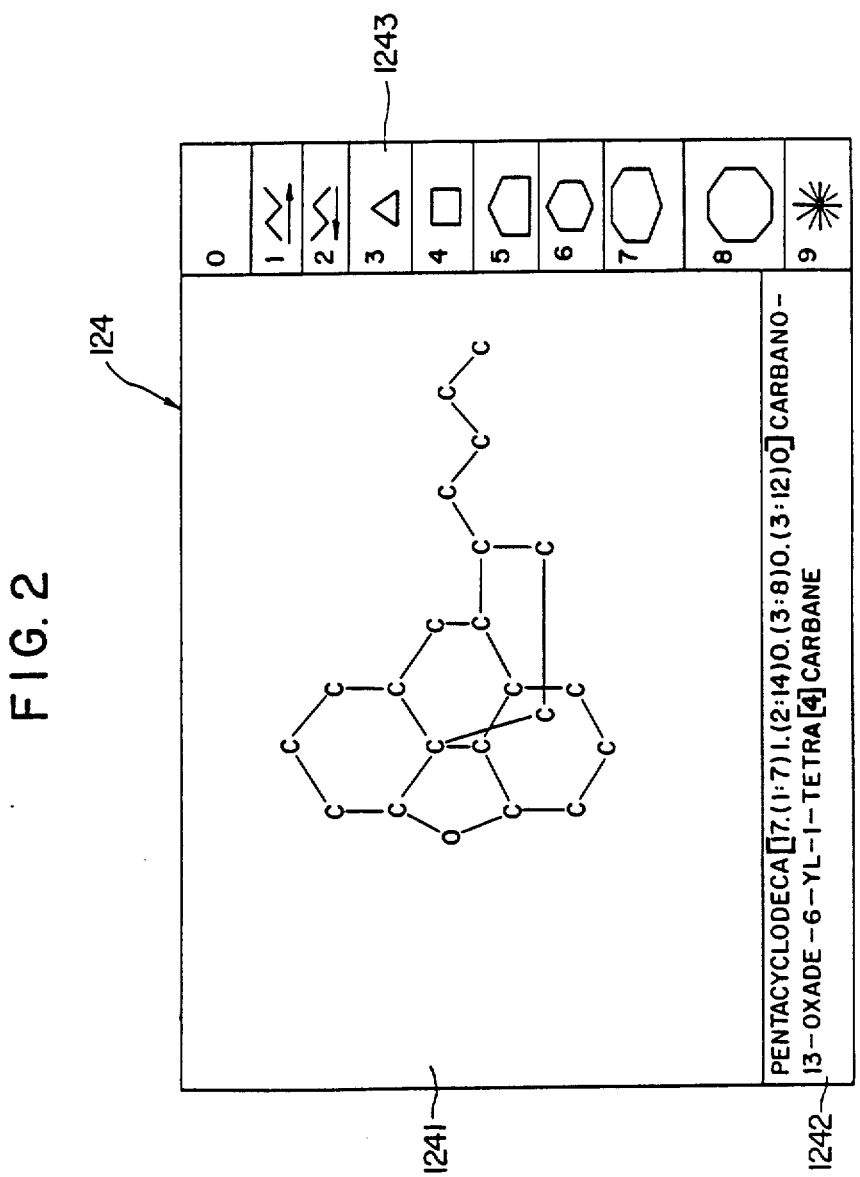
FIG. 2 is a fragmentary illustration of a display on a naming system of FIG. 1, which shows how data entry may be performed graphically.

FIG. 2 shows an example of a display 124 adapted for graphic input. As seen in FIG. 2, during graphic input mode, the display 124 is divided into a major area 1241 in which the chemical formula input is displayed, a text line 1242 in which the name of the compound in accordance with the present invention is displayed, and a column 1243 showing the various possible segments of chemical compounds which may be selected to form the input chemical formula.

The table storage 136 stores various tables, i.e. Tables 5 to 31-2 as disclosed later, used in implementing the computerized notation process according to the present invention. The tables are accessed during the naming process according to a notation program which will be set out with reference to FIG. 4 later.

Figure 3:
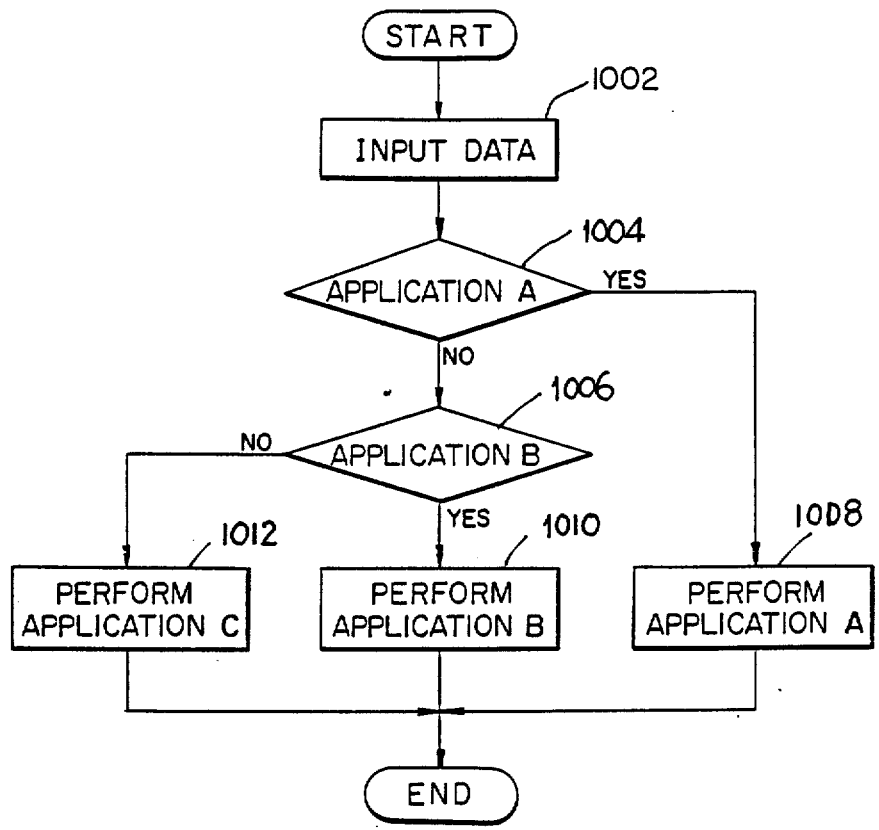
FIG. 3 is a flowchart of operation of the preferred embodiment of the naming system.

Before describing the computerized notation process of FIG. 4, a general discussion concerning application of the system of FIG. 1 will be briefly described with reference to FIG. 3, in which the general flowchart of selection of application mode of the system of FIG. 1 is illustrated. In the shown general flow, the graphic input and text input can be done in a step 1002. Depending on the type of input and according to the demand contained in input, the system performs three modes, i.e. APPLICATION A, APPLICATION B AND APPLICATION C, of operations. Mode selection is performed at steps 1004 and 1006.

Application mode A (step 1008) is adapted to perform index search for locating similar structure of a chemical compound in the already known compounds which data is stored in the data storage. In order to enter the operation in Application mode A, the text input 114 is performed for entry of the name given by the notation process according to the invention.

Application mode B (step 1010) is to give a name for a newly developed chemical compound. In this case, the chemical formula of the compound is entered by the graphic input 112.

Application mode C (step 1012) is adapted to access the chemical formula by inputting the already known name of the chemical compound.

One of the aforementioned nodes can be selected by inputting a command through the text input 1002.

Figure 4:
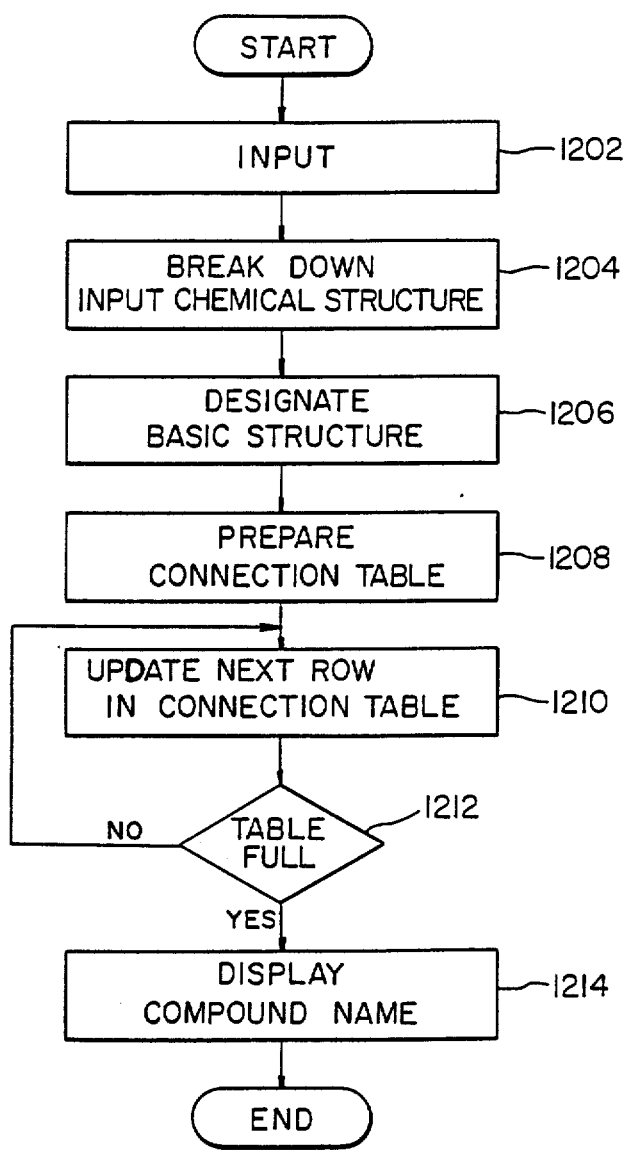
FIG. 4 is a flowchart of a program for determining the name of a chemical compound.

FIG. 4 is a flowchart of the notation program which assigns names to chemical compounds according to the preferred process as set out above. In the preferred embodiment, the chemical structure is input graphically immediately after starting execution, at a step 1202. The input chemical structure is broken down at a step 1204 into its individual constituent elements, radicals and carbon groups, according to which the fundamental structure is classified into one of the groups set out in the foregoing sub-sections 1 to 5, at a step 1206. According to the classification of the fundamental structure derived in the step 1206, a connection table, examples of which have been shown in FIGS. 5-1(A) to 5-5(I), is prepared at a step 1208.

Figures 5, 5A:
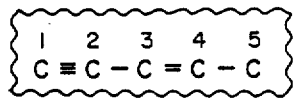
Figures 5, 5B:
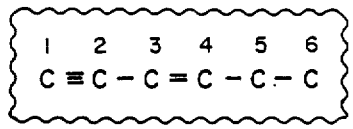
Figures 5, 5C:
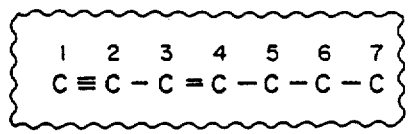
Figures 5, 5D:
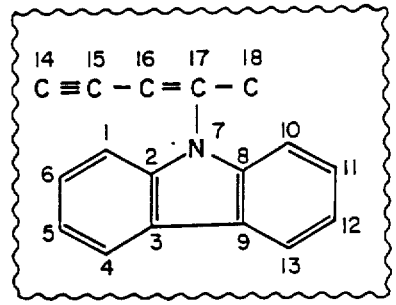
Figures 5, 5E:
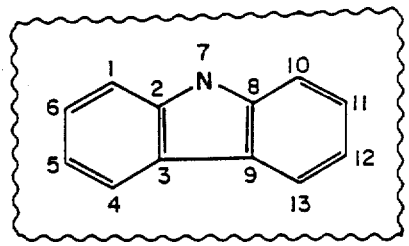
Figures 5, 5F:
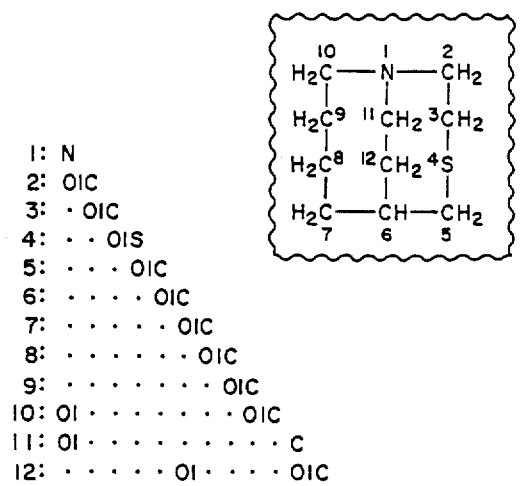
Figures 5, 5H:
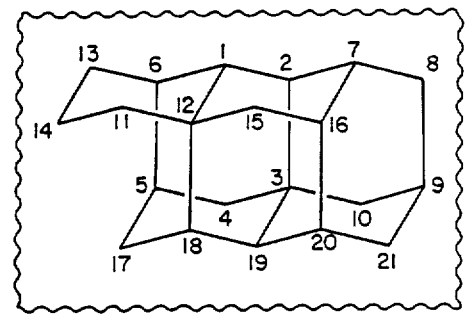
Figure 5:
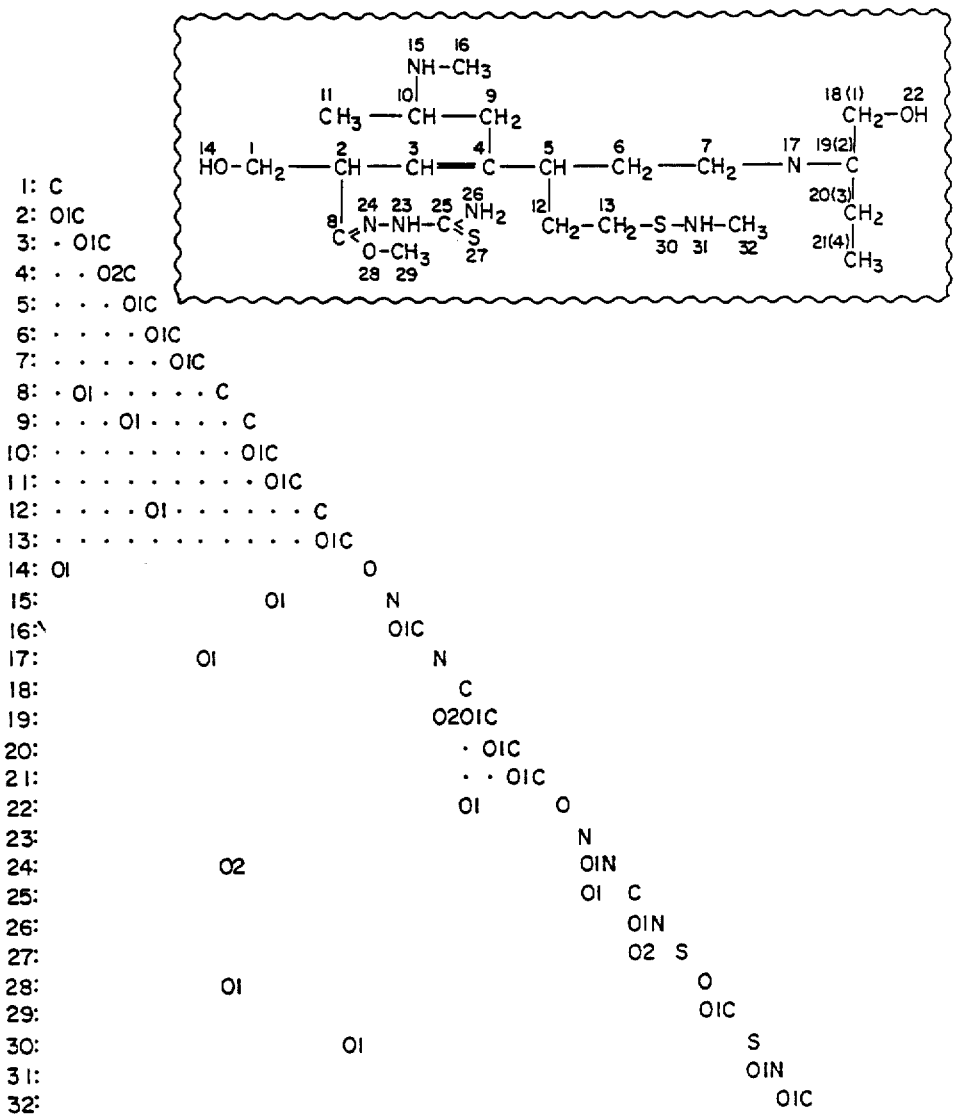

It should be noted that, in FIGS. 5-1(A) to 5-5(I), the number of the table identifies the numbering of atoms other than hydrogen atoms in the object compound. The order to number is standerized according to the predetermined rule, so that, a canonical connection table can be obtained. As will be seen from FIGS. 5-1(A) to 5-5(I), more than one connection table can be usually established for the object compound, because the order to number and traditional nomenclature rule are not related. For example, in the case of an aromatic compound, deletion or insertions of node are needed, so that, although they are analog compounds, they begin to have different node numbers. This is exemplified in FIG. 5-1(B). In order to avoid this, blank-nodes are used as shown in FIG. 5-1(A).

Connection tables are essentially triangular matrices with rows and columns both being assigned to each of the non-hydrogen elements of the compound. The cells at which the row and column indices match identify the element at that point, e.g. the 1—1 cell reads "c", meaning a carbon atom. The remaining columns for each row designate the presence or absence of a connection between the row-indexed element and the column-indexed element and the strength of the connection (+1 means a single bond and so forth). This is explained in greater detail later.

Step 1210 prepares one row of the connection table from the input formula. Step 1212 checks to see if the last row, i.e. the last major atom, has been completed and if not, returns control to step 1210 to fill in the next row. The steps 1210 and 1212 are repeated until all of the major components have been identified and cross-connected and entered into the connection table.

After the connection table is completed by repeating the steps 1210 and 1212, the resultant name is derived according to the inventive nomenclature system and displayed on the text line 1242 of the display 124 or, alternatively, output as a print-out by the printer 122.

The procedure for preparation of the connection table is disclosed in sub-section 9, in which tables stored in the table storage 136 are also illustrated.

9. The method of preparation of the connection table for the computer processing Using the name on this nomenclature system, the connection table which is usually used for the computer graphics of the organic compounds can be prepared by the following method.

The connection table has the form of a zero matrix which has plural rows and columns. All matrix elements other than the diagonal matrix elements are used to mean the bonding number between an atom and another atom, and the diagonal matrix elements are used to mean the species of the atoms.

Each matrix row number relates to the sequential number of the atom of the organic compound which is to be treated by this method (other than the hydrogens) and is given in the following process. Each matrix column number is also given.

The process is carried out in the order of the name of the components (previous section 2) in the complete name of the compound.

Making the full connection table becomes an easy way to convert the name of the components to each connection table.

To simplify this explanation, the following variables are used.

[X, Y]: the matrix element X-th row, Y-th column
[A] to [W]: variables described previous sections
a: a-th element of variable [D]
b: maximum number of element of variable [D]
c: c-th element of variable [E]
d: maximum number of element of variable [E]
x: variable to use calculation, means that processing is carried about x-th element of variable [D] or variable [E]
TN(xx,yy) means $$\sum_{xx=1}^{yy} Wx.$$

xx: value of start
yy: value of final

The method of converting the fundamental skeleton to the matrix must be selected by the case of variables-combination according to the table 5.

TABLE 5

| variable [A] | variable [B] | meaning | method |
|---|---|---|---|
| none | "AN" | group-I | (1) |
| "CYCLO" | "AN" | group-II | (2) |
| none | "AREN" | group-III | (3) |
| "CYCLO" | "AREN" | group-IV | (4) |

(1) The method (1)

[X, Y] and the value of the matrix element are given according to the table 6 using variable [E] of which element has the form ($R^c$Wc).

TABLE 6

| value of X | value of Y | value of [X, Y] |
|---|---|---|
| from 2 to TN(c=1,d) | X−1 | 1 |
| TN(c=1,x) $1<=x<=c-1$ | X−1 | 0 |
| 1+TN(c−1,x) $2<=x<=c$ | X−1 | 1 |

(2) The method (2)

[X, Y] and the value of the matrix element are given according to the table 7 using variable [D] of which element has the form ($R^{a:Sa}$Wc).

TABLE 7

| value of X | value of Y | value of [X, Y] |
|---|---|---|
| from 2 to TN(a=1,b) | X−1 | 1 |
| 1+TN(a=1,x) $1<=x<=c-1$ | X−1 | 0 |
| $W_1$ | 1 | 1 |
| TN(a=1,x) $2<=x<=b$ | Rx | 1 |
| Sx $2<=x<=b$ | TN(a=1,x) | 1 |

(3) The method (3)

[X, Y] and the value of the element are given according to the information of variable [E] of which the element has the form ($U^{c\cdot U^c}$, $V^c$Wc).

In any case of group-III, the first element which means c=1 should be done according to the table 8.

TABLE 8

| value of X | value of Y | value of [X, Y] |
|---|---|---|
| 6 | 1 | 9 |
| from 2 to 6 | X−1 | 9 |
| from 8(y−1)+2 to 8(y−1)+4 $2<=y<=W_1$ | X−1 | 9 |
| 8(y−1)+1 $2<=y<=W_1$ | X−7 | 9 |
| 8(y−1)+4 $2<=y<=W_1$ | X−9 | 9 |

Next processing is selected according to the value of Vc, and then the value of c is from 2 to d, so that the range of x is from 2 to d.

1st processing is according to the table 9.

TABLE 9

| Ux | value of X | | value of Y | value of [X,Y] |
|---|---|---|---|---|
| "A" | 8TN(C = 1, x − 1) + 8y + 2 | $0 < = y < = Wx - 1$ | X − 1 | 9 |
| | 8TN(C = 1, x − 1) + 8y + 1 | $1 < = y < = Wx - 1$ | X − 7 | 9 |
| | 8TN(C = 1, x − 1) + 6 | | X − 5 | 9 |
| "B" | 8TN(C = 1, x − 1) + 8y + 6 | $0 < = y < = Wx - 1$ | X − 5 | 9 |
| | 8TN(C = 1, x − 1) + 8y + 2 | $1 < = y < = Wx - 1$ | X − 1 | 9 |
| | 8TN(C = 1, x − 1) + 8y + 3 | $1 < = y < = Wx - 1$ | X − 1 | 9 |
| | 8TN(C = 1, x − 1) + 8y + 3 | $1 < = y < = Wx - 1$ | X − 9 | 9 |
| | 8TN(C = 1, x − 1) + 8y + 6 | $1 < = y < = Wx - 1$ | X − 9 | 9 |
| "C" | 8TN(C = 1, x − 1) + 8y + 2 | $0 < = y < = Wx - 1$ | X − 1 | 9 |
| | 8TN(C = 1, x − 1) + 8y + 6 | $0 < = y < = Wx - 1$ | X − 5 | 9 |
| | 8TN(C = 1, x − 1) + 8y + 6 | $0 < = y < = Wx - 1$ | X − 1 | 9 |
| | 8TN(C = 1, x − 1) + 8y + 5 | $1 < = y < = Wx - 1$ | X − 7 | 9 |
| | 8TN(C = 1, x − 1) + 8y + 2 | $1 < = y < = Wx - 1$ | X − 9 | 9 |
| "D" | 8TN(C = 1, x − 1) + 2 | | x − 1 | 9 |
| | 8TN(C = 1, x − 1) + 8y + 6 | $0 < = y < = Wx - 1$ | X − 5 | 9 |
| | 8TN(C = 1, x − 1) + 8y + 6 | $0 < = y < = Wx - 1$ | X − 1 | 9 |
| | 8TN(C = 1, x − 1) + 8y + 5 | $1 < = y < = Wx - 1$ | X − 1 | 9 |
| | 8TN(C = 1, x − 1) + 8y + 1 | $1 < = y < = Wx - 1$ | X − 3 | 9 |
| | 8TN(C = 1, x − 1) + 8y + 4 | $1 < = y < = Wx - 1$ | X − 7 | 9 |
| "E" | 8TN(C = 1, x − 1) + 4 | | X − 1 | 9 |
| | 8TN(C = 1, x − 1) + 8y + 6 | $1 < = y < = Wx - 1$ | X − 5 | 9 |
| | 8TN(C = 1, x − 1) + 8y + 6 | $0 < = y < = Wx - 1$ | X − 1 | 9 |
| | 8TN(C = 1, x − 1) + 8y + 5 | $0 < = y < = Wx - 1$ | X − 1 | 9 |
| | 8TN(C = 1, x − 1) + 8y + 1 | $1 < = y < = Wx - 1$ | X − 3 | 9 |
| | 8TN(C = 1, x − 1) + 8y + 4 | $1 < = y < = Wx - 1$ | X − 7 | 9 |
| "F" | 8TN(C = 1, x − 1) + 8y + 4 | $0 < = y < = Wx - 1$ | X − 1 | 9 |
| | 8TN(C = 1, x − 1) + 8y + 5 | $0 < = y < = Wx - 1$ | X − 1 | 9 |
| | 8TN(C = 1, x − 1) + 8y + 6 | $1 < = y < = Wx - 1$ | X − 1 | 9 |

TABLE 9-continued

| Ux | value of X | | value of Y | value of [X,Y] |
|---|---|---|---|---|
| | 8TN(C = 1, x − 1) + 8y + 3 | 1 < = y < = Wx − 1 | X − 7 | 9 |
| | 8TN(C = 1, x − 1) + 8y + 6 | 1 < = y < = Wx − 1 | X − 9 | 9 |
| "G" | 8TN(C = 1, x − 1) + 8y + 3 | 1 < = y < = Wx − 1 | X − 1 | 9 |
| | 8TN(C = 1, x − 1) + 8y + 4 | 0 < = y < = Wx − 1 | X − 1 | 9 |
| | 8TN(C = 1, x − 1) + 8y + 5 | 0 < = y < = Wx − 1 | X − 1 | 9 |
| | 8TN(C = 1, x − 1) + 8y + 6 | 1 < = y < = Wx − 1 | X − 1 | 9 |
| | 8TN(C = 1, x − 1) + 8y + 2 | 1 < = y < = Wx − 1 | X − 7 | 9 |
| | 8TN(C = 1, x − 1) + 8y + 5 | 1 < = y < = Wx − 1 | X − 9 | 9 |
| "H" | 8TN(C = 1, x − 1) + 8y + 4 | 0 < = y < = Wx − 1 | X − 1 | 9 |
| | 8TN(C = 1, x − 1) + 8y + 4 | 1 < = y < = Wx − 1 | X − 9 | 9 |
| | 8TN(C = 1, x − 1) + 5 | | X − 1 | 9 |

2nd processing is selected by the case of value Vx according to table 10.

TABLE 10

| value of Vx | method |
|---|---|
| "A" | (a) |
| "B" or "C" | (b) |
| "D" | (d) |
| "E" | (e) |
| "F" or "G" | (f) |
| "H" | (h) |

The method (a)

If Wx=U'x then the connection table is completed according to the table 11, and in other cases the processing is continued after treating of table 11.

TABLE 11

| case | value of X | | value of Y | value of [X, Y] |
|---|---|---|---|---|
| U' x > = 2 | 8TN(c = 1, x − 1) + y | 5 < = y < = 6 | X − 1 | 9 |
| | 8TN(c = 1, x − 1) + 8y + 3 | 0 < = y < = U' x − 2 | X − 1 | 9 |
| | 8TN(c = 1, x − 1) + 8y + 4 | 0 < = y < = U' x − 2 | X − 1 | 9 |
| | 8TN(c = 1, x − 1) + 8y + 4 | 1 < = y < = U' x − 1 | X − 9 | 9 |
| | 8TN(c = 1, x − 1) + 8(U' x − 2) + 3 | | 8Ux − 2 | 9 |
| | 8TN(c = 1, x − 1) + 8(U' x − 1) + 2 | | 8Ux − 7 | 9 |
| U' x = 1 | 8TN(c = 1, x − 1) + 6 | | X − 7 | 9 |
| | 8TN(c = 1, x − 1) + 2 | | 8Ux − 7 | 9 |
| | 8TN(c = 1, x − 1) + 5 | | 8Ux − 2 | 9 |
| U' x = 0 | 8TN(c = 1, x − 1) + 6 | | 8Ux − 7 | 9 |

If Ux=TN(c=1, x−1) then the connection table is completed by the method according to the table 12. And in other cases the table 12 is not used.

TABLE 12

| value of X | | value of Y | value of [X,Y] |
|---|---|---|---|
| 8TN(c = 1, x − 1) + 8y + 3 | U' x < = y < = Wx − 1 | X − 1 | 9 |
| 8TN(c = 1, x − 1) + 8y + 4 | U' x + 1 < = y < = Wx − 1 | X − 1 | 9 |
| 8TN(c = 1, x − 1) + 8y + 4 | U' x + 1 < = y < = Wx − 1 | X − 9 | 9 |
| 8TN(c = 1, x − 1) + 8U' x + 3 | | 8Ux − 6 | 9 |

If 8TN(c=1, x−1)−Ux> =Wx−U'x then the processing is done according to table 13 and in another case according to Table 14.

TABLE 13

| Value of X | Value of Y | Value of [X, Y] |
|---|---|---|
| 8TN(c = 1, x − 1) + 8y + 2<br>U' x < = y < = Wx − 1 | 8(Ux + y) + 1 | 9 |

TABLE 14

| Value of X | Value of Y | Value of [X,Y] |
|---|---|---|
| 8TN(c = 1, x − 1) + 8y + 2<br>U' x < = y < = 8TN(c = 1, x − 1) − Ux + U' x | 8(Ux + y) + 1 | 9 |
| 8TN(c = 1, x − 1) + 8y + 3<br>8TN(c = 1, x − 1) − Ux + U' x < = y < = Wx − 1 | X − 1 | 9 |
| 8TN(c = 1, x − 1) + 8y + 4<br>8TN(c = 1, x − 1) − Ux + U' x + 1 < = y < = Wx − 1 | X − 1 | 9 |
| 8TN(c = 1, x − 1) + 8y + 3<br>y = 8TN(c = 1, x − 1) − Ux + U' x | 8TN(c = 1, x − 1) − 6 | 9 |

The method (b).

[X, Y] and the value of the matrix are given by the case of value of Ux and U'x such as table 15.

TABLE 15

| Case | Value of X | Value of Y | Value of [X, Y] |
|---|---|---|---|
| $U'x >= 1$ | $8TN(c = 1, x - 1) + 6$ | $X - 1$ | 9 |
|  | $8TN(c = 1, x - 1) + 5$ | $8Ux - 2$ | 9 |
|  | $8TN(c = 1, x - 1) + 2$ | $8Ux - 7$ | 9 |
| $Ux = 8TN(c = 1, x - 1)$ | $8TN(c = 1, x - 1) + 3$ | $X - 1$ | 9 |
|  | $8TN(c = 1, x - 1) + 4$ | $8Ux - 6$ | 9 |
|  | $8TN(c = 1, x - 1) + 6$ | $8Ux - 7$ | 9 |
| $U'x = 0$ and | $8TN(c = 1, x - 1) + 6$ | $8Ux - 7$ | 9 |
| $Ux < 8TN(c = 1, x - 1)$ | $8TN(c = 1, x - 1) + 2$ | $8Ux + 1$ | 9 |

The method (d)

[X, Y] and the value of the matrix element are given according to table 16.

TABLE 16

| Value of X | Value of Y | Value of [X, Y] |
|---|---|---|
| $8TN(c = 1, x - 1) + 3$ | $X - 9$ | 9 |
| $8TN(c = 1, x - 1) + 4$ | $X - 6$ | 9 |

The method (e)

[X, y] and the value of the matrix element are given according to the table 17.

TABLE 17

| Value of X | Value of Y | Value of [X, Y] |
|---|---|---|
| $8TN(c = 1, x - 1) + 1$ | $X - 4$ | 9 |
| $8TN(c = 1, x - 1) + 2$ | $X - 6$ | 9 |

The method (f)

[X, Y] and the value of the matrix are given by the case of value of Ux and U'x such as table 18.

TABLE 18

| Case | Value of X | Value of Y | Value of [X, Y] |
|---|---|---|---|
| $U'x >= 1$ | $8TN(c = 1, x - 1) + 6$ | $X - 1$ | 9 |
|  | $8TN(c = 1, x - 1) + 6$ | $8Ux - 3$ | 9 |
|  | $8TN(c = 1, x - 1) + 3$ | $8Ux - 4$ | 9 |
| $Ux = 8TN(c = 1, x - 1)$ | $8TN(c = 1, x - 1) + 3$ | $X - 1$ | 9 |
|  | $8TN(c = 1, x - 1) + 2$ | $8Ux - 5$ | 9 |
|  | $8TN(c = 1, x - 1) + 5$ | $8Ux - 4$ | 9 |
| $U'x = 0$ and | $8TN(c = 1, x - 1) + 6$ | $8Ux - 4$ | 9 |
| $Ux < 8TN(c = 1, x - 1)$ | $8TN(c = 1, x - 1) + 2$ | $8Ux + 4$ | 9 |

The method (h)

If $Wx = U'x$ then the connection table is complicated according to the table 19, and in other cases the processing is continued after treating of table 19.

TABLE 19

| Case | Value of X | Value of Y | Value of [X, Y] |
|---|---|---|---|
| $U'x >= 2$ | $8TN(c = 1, x - 1) + 6$ | $X - 5$ | 9 |
|  | $8TN(c = 1, x - 1) + 6$ | $X - 1$ | 9 |
|  | $8TN(c = 1, x - 1) + 8y + 3 \ 0 <= y <= U'x - 2$ | $X - 1$ | 9 |
|  | $8TN(c = 1, x - 1) + 8y + 2 \ 0 <= y <= U'x - 2$ | $X - 1$ | 9 |
|  | $8TN(c = 1, x - 1) + 8y + 1 \ 1 <= y <= U'x - 1$ | $X - 7$ | 9 |
|  | $8TN(c = 1, x - 1) + 8(U'x - 2) + 2$ | $8Ux - 3$ | 9 |
|  | $8TN(c = 1, x - 1) + 8(U'x - 1) + 3$ | $8Ux - 4$ | 9 |
| $U'x = 1$ | $8TN(c = 1, x - 1) + 6$ | $X - 1$ | 9 |
|  | $8TN(c = 1, x - 1) + 6$ | $8Ux - 3$ | 9 |
|  | $8TN(c = 1, x - 1) + 3$ | $8Ux - 4$ | 9 |
| $U'x = 0$ | $8TN(c = 1, x - 1) + 5$ | $8Ux - 4$ | 9 |

If $Ux = TN(c = 1, x - 1)$ then the connection table is complicated by the method according to the table 20. And in other cases the table 20 is neglected.

TABLE 20

| Value of X | Value of Y | Value of [X, Y] |
|---|---|---|
| $8TN(c = 1, x - 1) + 8y + 3 \ U'x <= y <= Wx - 1$ | $X - 1$ | 9 |
| $8TN(c = 1, x - 1) + 8y + 2 \ U'x + 1 <= y <= Wx - 1$ | $X - 1$ | 9 |
| $8TN(c = 1, x - 1) + 8y + 1 \ U'x + 1 <= y <= Wx - 1$ | $X - 7$ | 9 |
| $8TN(c = 1, x - 1) + 8U'x + 2$ | $8Ux - 5$ | 9 |

If $8TN(c = 1, x - 1) - Ux >= Wx - U'x$ then the processing is done according to table 21 and in another case according to table 22.

TABLE 21

| Value of X | Value of Y | Value of [X, Y] |
|---|---|---|
| 8TN(c = 1,x − 1) + 8y + 3 U'x <= y <= Wx − 1 | 8(Ux + y) + 4 | 9 |

TABLE 22

| Value of X | Value of Y | Value of [X, Y] |
|---|---|---|
| 8TN(c = 1,x − 1) + 8y + 3<br>U'x <= y <= 8TN(c = 1,x − 1) − Ux + U'x | 8(Ux + y) + 4 | 9 |
| 8TN(c = 1,x − 1) + 8y + 3<br>8TN(c = 1,x − 1) − Ux + U'x <= y <= Wx − 1 | X − 1 | 9 |
| 8TN(c = 1,x − 1) + 8y + 2<br>8TN(c = 1,x − 1) − Ux + U'x + 1 <= y <= Wx − 1 | X − 1 | 9 |
| 8TN(c = 1,x − 1) + 8y + 1<br>8TN(c = 1,x − 1) − Ux + U'x + 1 <= y <= Wx − 1 | X − 7 | 9 |
| 8TN(c = 1,x − 1) + 8y + 2<br>y = 8TN(c = 1,x − 1) − Ux + U'x | 8TN(c = 1,x − 1) − 5 | 9 |

(4) The method (4)

[X, Y] and the value of the matrix element are given by the information of variable [D] of which the element has the form [Ra:Sa$_{Wa}$] and variable [E] of which the element has the form (Vc).

In this case variable [z] is used, and z means z-th element of variable [E].

$$1 <= z <= d$$

At first, the processing is done according to the table 23.

TABLE 23

| Value of X | Value of Y | Value of [X,Y] |
|---|---|---|
| 6 | 1 | 9 |
| y 6 <= y <= 5 | X − 1 | 9 |
| 8(z − 1) + 4 1 <= y <= d | X − 1 | 9 |
| 8(z − 1) + 3 1 <= z <= d | X − 1 | 9 |
| 8(z − 1) + 2 1 <= z <= d | X − 1 | 9 |
| 8TN(a − 1,x) − 2 1 <= x <= b | X − 1 | 0 |
| 8TN(a = 1,x) − 3 1 <= x <= b | X − 1 | 0 |
| 8TN(a = 1,x) − 4 1 <= x <= b | X − 1 | 0 |
| 8TN(a = 1,x − 1) + 2 2 <= x <= b | X − 1 | 0 |
| 8TN(a = 1,x − 1) + 3 2 <= x <= b | X − 1 | 0 |
| 8TN(a = 1,x − 1) + 4 2 <= x <= b | X − 1 | 0 |

2nd processing is selected by the value of the Vz according to the table 25. But in the case of following values of z, the processing may not be done.

z = 8TN(a = 1, x) + 1, 1 <= x <= b − 1
z = 8TN(a = 1, x), 1 <= x <= b

TABLE 25

| Value of Vz | Value of X | Value of Y | Value of [X, Y] |
|---|---|---|---|
| "V" | 8z + 1 | 8z − 7 | 9 |
|  | 8z + 4 | 8z − 6 | 9 |
| "P" | 8x + 1 | 8z − 6 | 9 |
|  | 8z + 4 | 8z − 5 | 9 |
| "M" | 8z + 1 | 8z − 5 | 9 |
|  | 8z + 4 | 8z − 4 | 9 |

The processing is done about 1st-Wx according to table 26.

TABLE 26

| Value of Vz | Value of Vz | Value of X | Value of Y | Value of [X, Y] |
|---|---|---|---|---|
| "V" | every case | 8z − 4 | 8z − 5 | 9 |
|  |  | 8z − 4 | 5 | 9 |
|  | "V" | 8z − 7 | 8z − 15 | 0 |
|  |  | 8z − 15 | 6 | 9 |
|  | "P" | 8z − 7 | 8z − 14 | 0 |
|  |  | 8z − 14 | 6 | 9 |
|  | "M" | 8z − 7 | 8z − 13 | 0 |
|  |  | 8z − 13 | 6 | 9 |
| "P" | every case | 8z − 7 | 6 | 9 |
|  |  | 8z − 4 | 5 | 9 |
| "M" | every case | 8z − 6 | 8z − 7 | 9 |
|  |  | 8z − 6 | 6 | 9 |
|  | "V" | 8z − 4 | 8z − 14 | 0 |
|  |  | 8z − 14 | 5 | 9 |
|  | "P" | 8z − 4 | 8z − 13 | 0 |
|  |  | 8z − 13 | 5 | 9 |
|  | "M" | 8z − 4 | 8z − 12 | 0 |
|  |  | 8z − 12 | 5 | 9 |

In the case Wx = 0, the processing is done according to the table 27.

TABLE 27

| Value of V$_{Sx}$ | Value of X | Value of Y | Value of [X, Y] |
|---|---|---|---|
| every case | 8Sx − 4 | 8Sx − 5 | 0 |
|  | 8Sx − 5 | 8Sx − 6 | 0 |
|  | 8Sx − 6 | 8Rx − 4 | 9 |
| "V" | 8Sx − 4 | 8Sx − 14 | 0 |
|  | 8Sx − 14 | 8Rx − 5 | 9 |
| "P" | 8Sx − 4 | 8Sx − 13 | 0 |
|  | 8Sx − 13 | 8Rx − 5 | 9 |
| "M" | 8Sx − 4 | 8Sx − 12 | 0 |
|  | 8Sx − 12 | 8Rx − 5 | 9 |

In the case Wx = 1, the processing is done according to the table 28 or the table 29.

If R'x is none then the processing is done according to the table 28-1 and the table 28-2.

TABLE 28-1

| Value of S'x | Value of V$_{TN(a=1,x)}$ | Value of X | Value of Y | Value of [X,Y] |
|---|---|---|---|---|
| none | "V" | 8Sx − 4 | 8Rx − 5 | 9 |
|  |  | 8TN(a = 1,x) − 5 | 8Sx − 5 | 9 |
|  |  | 8TN(a = 1,x) − 4 | 8TN(a = 1,x) − 5 | 9 |
|  |  | 8TN(a = 1,x) − 4 | 8Rx − 4 | 9 |
|  | "P" | 8TN(a = 1,x) − 7 | 8Rx − 5 | 9 |
|  |  | 8TN(a = 1,x) − 7 | 8Sx − 4 | 9 |

TABLE 28-1-continued

| Value of S'x | Value of $V_{TN(a=1,x)}$ | Value of X | Value of Y | Value of [X,Y] |
|---|---|---|---|---|
| | | 8TN(a=1,x)−4 | 8Rx−4 | 9 |
| | | 8TN(a=1,x)−4 | 8Sx−5 | 9 |
| | "M" | 8TN(a=1,x)−7 | 8Rx−5 | 9 |
| | | 8TN(a=1,x)−6 | 8TN(a−1,x)−7 | 9 |
| | | 8TN(a=1,x)−6 | 8Sx−4 | 9 |
| | | 8Sx−5 | 8Rx−4 | 9 |

TABLE 28-2

| Value of S'x | Value of $V_{TN(a=1,x)}$ | Value of $V_{Sx}$ | Value of X | Value of Y | Value of [X,Y] |
|---|---|---|---|---|---|
| Sx+1 | "V" | every case | 8TN(a=1,x)−4 | 8S'x−4 | 9 |
| | | | 8TN(a=1,x)−4 | 8Rx−4 | 9 |
| | | "V" | 8Sx−5 | 8Rx−5 | 9 |
| | | "P" | 8Sx−4 | 8Rx−5 | 9 |
| | "P" | every case | 8TN(a=1,x)−7 | 8Rx−5 | 9 |
| | | | 8S'x−4 | 8Rx−4 | 9 |
| | | "V" | 8TN(a=1,x)−7 | 8Sx−5 | 9 |
| | | "P" | 8TN(a=1,x)−7 | 8Sx−4 | 9 |

If S'x is none then the processing is done according to the table 29.

TABLE 29

| Value of R'x | Value of VTN (a=1,x) | Value of VRx | Value of X | Value of Y | Value of [X,Y] |
|---|---|---|---|---|---|
| Rx+1 | "P" | every case | 8R'x−4 | 8Sx−4 | 9 |
| | | | 8TN(a=1,x)−3 | 8Sx−5 | 9 |
| | | "V" | 8TN(a=1,x)−3 | 8Rx−5 | 9 |
| | | "P" | 8TN(a=1,x)−3 | 8Rx−4 | 9 |
| | "M" | every case | 8TN(a=1,x)−6 | 8Sx−4 | 9 |
| | | | 8TN(a=1,x)−6 | 8R'x−4 | 9 |
| | | "V" | 8Sx−4 | 8Rx−5 | 9 |
| | | "P" | 8Sx−4 | 8Rx−4 | 9 |

In the case Wx > =2, the processing is done according to following tables.

The table 30-1 is applied to the processing of {TN(a=1, x−1)+1}th Vz, where 2> =x> =b and R'x is none, and if R'x=Rx+1 then according to the table 30-2.

TABLE 30-1

| Value of R'x | Value of $V_{TN(a=1,x-1)+1}$ | Value of X | Value of Y | Value of [X,Y] |
|---|---|---|---|---|
| none | every case | 8TN(a=1,x−1)+4 | 8TN(a=1,x−1)+3 | 9 |
| | | 8TN(a=1,x−1)+3 | 8TN(a=1,x−1)+2 | 9 |
| | | 8TN(a=1,x−1)+2 | 8TN(a=1,x−1)+1 | 9 |
| | | 8TN(a=1,x−1)+4 | Rx−4 | 9 |
| | | 8TN(a=1,x−1)+1 | Rx−5 | 9 |
| | "V" | 8TN(a=1,x−1)+1 | 8TN(a=1,x−1)+9 | 9 |
| | | 8TN(a=1,x−1)+2 | 8TN(a=1,x−1)+12 | 9 |
| | "P" | 8TN(a=1,x−1)+2 | 8TN(a=1,x−1)] | 9 |
| | | 8TN(a=1,x−1)+3 | 8TN(a=1,x−1)+12 | 9 |
| | "M" | 8TN(a=1,x−1)+3 | 8TN(a=1,x−1)+9 | 9 |
| | | 8TN(a=1,x−1)+4 | 8TN(a=1,x−1)+12 | 9 |

TABLE 30-2

| Value of R'x | Value of $V_{Rx}$ | Value of $V_{TN(a=1,x-1)+1}$ | Value of X | Value of Y | Value of [X, Y] |
|---|---|---|---|---|---|
| Rx+1 | every case | every case | 8TN(a=1, x−1)+4 | 8TN(a=1, x−1)+3 | 9 |
| | | | 8TN(a=1, x−1)+3 | 8TN(a=1, x−1)+2 | 9 |
| | | | 8TN(a=1, x−1)+2 | 8R'x−4 | 9 |
| | | "P" | 8TN(a=1, x−1)+2 | 8TN(a=1, x−1)+9 | 9 |
| | | | 8TN(a=1, x−1)+3 | 8TN(a=1, x−1)+12 | 9 |
| | | "M" | 8TN(a=1, x−1)+3 | 8TN(a=1, x−1)+9 | 9 |
| | | | 8TN(a=1, x−1)+4 | 8TN(a=1, x−1)+12 | 9 |
| | | "V" | 8TN(a=1, x−1)+4 | RX−5 | 9 |
| | | "N" | 8TN(a=1, X−1)+4 | RX−4 | 9 |

The table 31-1 is applied to the processing of {TN(a=1, x)th Vz, where 2> =x> =b and S'x is none, and if S'x=Sx+1 then according to the table 31-2.

TABLE 31-1

| Value of S'x | Value of $V_{Sx}$ | Value of $V_{TN(a=1,x)}$ | Value of X | Value of Y | Value of [X,Y] |
|---|---|---|---|---|---|
| none | "V" | every case | 8TN(a=1,x)−5 | 8Sx−4 | 9 |
| | | | 8TN(a=1,x)−4 | 8TN(a=1,x)−5 | 9 |
| | | "V" | 8TN(a=1,x)−7 | 8TN(a=1,x)−15 | 0 |
| | | | 8TN(a=1,x)−15 | 8Sx−5 | 9 |
| | | "P" | 8TN(a=1,x)−7 | 8TN(a=1,x)−14 | 0 |
| | | | 8TN(a=1,x)−14 | 8Sx−5 | 9 |

TABLE 31-1-continued

| Value of S'x | Value of V$_{Sx}$ | Value of V$_{TN(a=1,x)}$ | Value of X | Value of Y | Value of [X,Y] |
|---|---|---|---|---|---|
| | | "M" | 8TN(a=1,x)−7 | 8TN(a=1,x)−13 | 0 |
| | | | 8TN(a=1,x)−13 | 8Sx−5 | 9 |
| | "P" | | 8TN(a=1,x)−7 | 8Rx−4 | 9 |
| | | | 8TN(a=1,x)−4 | 8Rx−5 | 9 |
| | "M" | every case | 8TN(a=1,x)−6 | 8TN(a=1,x)−7 | 9 |
| | | | 8TN(a=1,x)−6 | 8Rx−4 | 9 |
| | | "V" | 8TN(a=1,x)−4 | 8TN(a=1,x)−14 | 0 |
| | | | 8TN(a=1,x)−13 | 8Sx−5 | 9 |
| | | "P" | 8TN(a=1,x)−4 | 8TN(a=1,x)−13 | 0 |
| | | | 8TN(a=1,x)−14 | 8Sx−5 | 9 |
| | | "M" | 8TN(a=1,x)−4 | 8TN(a=1,x)−12 | 0 |
| | | | 8TN(a=1,x)−12 | 8Sx−5 | 9 |

TABLE 31-2

| Value of S'x | Value of V$_{TN(a=1,x)}$ | Value of V$_{TN(a=1,x)−1}$ | Value of V$_{Sx}$ | Value of X | Value of Y | Value of [X,Y] |
|---|---|---|---|---|---|---|
| Sx+1 | "V" | every case | | 8TN(a=1,x)−4 | 8S'x−4 | 9 |
| | | | "V" | 8TN(a=1,x)−7 | 8TN(a=1,x)−15 | 0 |
| | | | "V" | 8TN(a=1,x)−15 | 8Sx−5 | 9 |
| | | | "P" | 8TN(a=1,x)−15 | 8Sx−4 | 9 |
| | | "P" | every case | 8TN(a=1,x)−7 | 8TN(a=1,x)−14 | 0 |
| | | | "V" | 8TN(a=1,x)−14 | 8Sx−5 | 9 |
| | | | "P" | 8TN(a=1,x)−14 | 8Sx−4 | 9 |
| | | "M" | every case | 8TN(a=1,x)−7 | 8TN(a=1,x)−13 | 0 |
| | | | "V" | 8TN(a=1,x)−13 | 8Sx−5 | 9 |
| | | | "P" | 8TN(a=1,x)−13 | 8Sx−5 | 9 |
| | "P" | every case | "V" | 8TN(a=1,x)−7 | 8Sx−5 | 9 |
| | | | "P" | 8TN(a=1,x)−7 | 8Sx−4 | 9 |
| | | "V" | every case | 8TN(a=1,x)−4 | 8TN(a=1,x)−14 | 0 |
| | | | "V" | 8TN(a=1,x)−14 | 8Sx−5 | 9 |
| | | | "P" | 8TN(a=1,x)−14 | 8Sx−4 | 9 |
| | | "P" | every case | 8TN(a=1,x)−4 | 8TN(a=1,x)−13 | 0 |
| | | | "V" | 8TN(a=1,x)−13 | 8Sx−5 | 9 |
| | | | "P" | 8TN(a=1,x)−13 | 8Sx−4 | 9 |
| | | "M" | every case | 8TN(a=1,x)−4 | 8TN(a=1,x)−12 | 0 |
| | | | "V" | 8TN(a=1,x)−12 | 8Sx−5 | 9 |
| | | | "P" | 8TN(a=1,x)−12 | 8Sx−4 | 9 |

EXAMPLES

1. The structures of 16 organic compounds and their names according to this nomenclature system are set forth immediately below as an illustration of the operation of this nomenclature system. The name of organic compounds of this nomenclature are following according to the FIG. 1.

1. deca[$7^3 1^4 2$]carbane
2. octa[$6^3 2$]carban-2-en-4-yne
3. octa[$6^2 1^4 1$]carban-4:8-ene
4. tricycloundeca[$11^{1:5} 0^{2:7} 0$]carbane
5. dicyclotrideca[$12^{1:7} 1$]carban-1,6,9-triene
6. undeca[$5^{1\cdot14} 1^{2C} 2^{8A} 1^{3G} 2$]arene
7. cycloocta[$8^M$]arene
8. dicyclohexacosa[$26^{1:13} 1$][$1 V_2^{PM} 3^{P} 2^{MP} 1 V_2 P_3^M 2 V_3^M 2^P .1^P$]arene
9. tetra[4]areno-$2^{6Z}$-homo-$3^4$-norade
10. tetra[4]areno-$2^4,3^4$-dinorade
11. hexa[6]areno-$1^6,2^4,3^4,4^4,5^4,6^4$-hexanor-$1^4$:$6^3$-cyclade
12. diareno-2:3-didehydrade
13. trideca[$5^{1,4} 4^{1,4} 4$]areno-$2^{2:3}$-seco-$5^{3Z}$-home-$1^6$-nor-$1^5,5^{2/3Z}$-tetrahydrade 14. tri[3]areno-1⁶,3⁴-dinor-1⁴,3¹-dihydro-1₁,3³-diaza-1⁴-selena-3¹-sulfade
15. dicycloheptadeca[16^{1:9}1]carbano-1,4,6,9,12,14-hexaaza-3,7,10,16-tetrasulfade
16. cyclooctacarbano-1-(azayl-2-dicarbano-1-ylazylcarbazantazent)

(1) 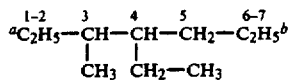

(2) 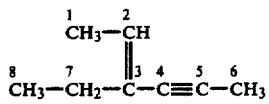

(3) 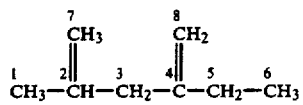

(4) 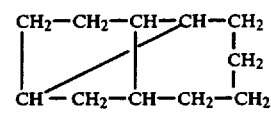

(5) 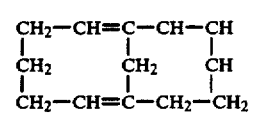

(6) 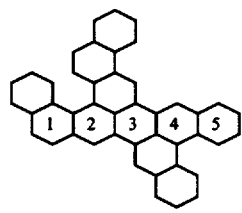

(7) 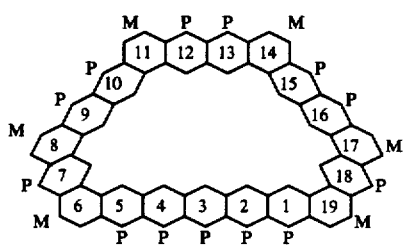

(8) 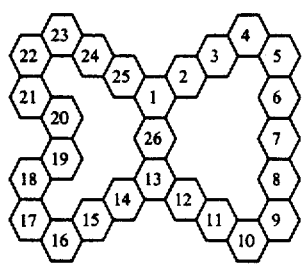

(9) 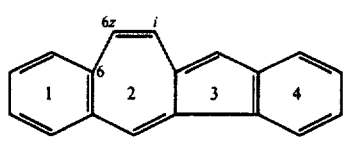

(10) 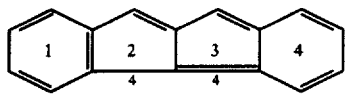

(11) 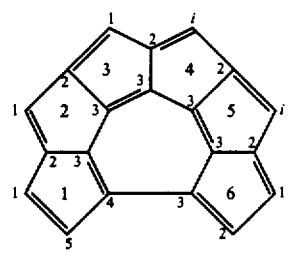

(12) 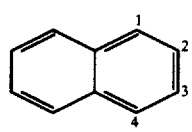

(13) 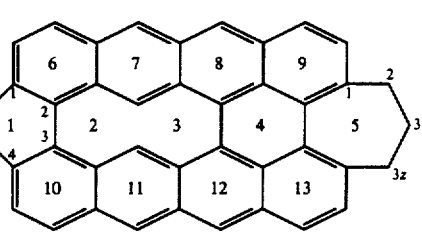

(14) 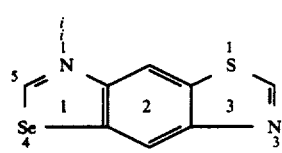

(15) 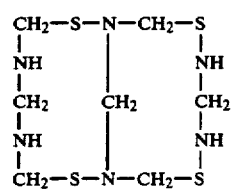

(16) 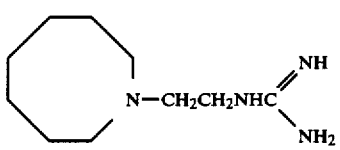

2. The structures of 35 pharmaceutical compounds and their names according to the present nomenclature system are set forth immediately below.

1: bi[dicarbano-1-chlorant[-2,2'-biylazcarbantoxent
2: tetra[4]carbano-1,4-diyloxylsulfbioxentcarbant
3: octa[5.²1.²1.³1]carbano-1,6-diyloxylcarbazantoxent
4: bi[cyclooctacarbano-1-(azayl-2-dicarbano-1-ylazylcarbazant-azent)]sulfate
5: ter[tricarbanoaza]-1,1',1"-terylphosphsulfent
6: cyclohexacarbano-1-aza-3-oxa-2-(phosphaoxentylazdiyl-2-dicarbano-1-chlorant)
7: dicyclodeca[6.¹:¹⁴]carbano-4,7,9-triaza-10-oxent-7-ylarene-4-yl-4-tetra[4]carbano-1-(oxentyl-4-areno-1-fluorant)

8: bi[norareno-1-(hydrosulfa)]-2,2'-biylcarbyliden-5-cyclohexacarbano-1-azaium-1,1-bicarbant-3-ylox-carbant 9: nordiareno-1/3-trihydro-1,3-diaza-2-oxent-1-yl-6-cyclohexa-carbano-1-(azayl-4-tetra[4]carbano-1,1-diyl-4-areno-1-fluorant)

10: bi[cyclopentacarbano-1-(azaiumcarbant)]-1,1'-biyl-1,3-tricarbane bi[tetra[4]carbano-1-acid-4-acidate-2,3-dioxant]

11: cyclopentacarbanoaza-2-oxent-1-yl-1-trideca[12.$^{6}$1]-carban-2,4,6-trieno-8-oxant-1-oxent 12: cyclohexacarbanen-3,5-diaza-1-fluorant-4,6-dioxent-3-yl-2-cyclopentacarbanooxade 13: bi[arenoyl-2-tricarbano-1-(acidoyl-6-dicyclooc-ta[7.$^{1:4}$1]-carbano-8-(azaiumcarbant))-3-oxant]sulfate 14: biarenobiyl-2,2-dicarbano-1-(acidoyl-6-tricyclododeca[7.$^{1:4}$1$^{8:8}$4]carbano-8-azaium)-2-oxant chloride 15: arenoyl-2-tricarbano-1-(acidoyl-7-tricyclonona[8.$^{1:5}$1.$^{2:4}$0]-carbano-9-azaium-3-oxa-9,9-dicarbant)-3-oxant bromide 16: dicycloocta[7.$^{1:4}$1]carbano-6-azaium-1,6,8,8-tetracarbant-6-yl-3-tricarbano-1-ylaziumtercarbant bi[-carbanoyloxysulfbiox-acidate]

17: decyclohepta[6.$^{1:4}$1]carbano-2,2,3-tricarbant-3-ylaz-carbant hydrochloride 18. diareno-1/4-tetrahydro-2,4-diaza-1-(sulfabioxent)-6-(ylcarb-terfluorant)-3-yl-1-hexa[6]carbane-7-ylsulfazantbioxent 19. disodium trinordiarenoperhydro-2Z-aza-5-sulfa-4,4-dicarbant-2-oxent-3-(ylcarbacidate)-1-ylazyl-2-dicarbano-2-oxent-1-ylarene-1-ylsulfbioxacidate 20: dinordiareno-1/2Z,5/6Z-hexahydro-2Z-aza-6-sulfa-4-carbant-2-oxent-1-(ylazyl-2-dicarbano-1-azant-2-oxent-1-ylarene)-3-ylcarbacid 21: diareno-1,3,5,8-tetraaza-2,4-diazant-6-ylcar-bylazacarbant-yl-4-areno-1-ylcarboxentylazyl-2-penta[5]carbano-1,5-diacid 22: diareno-2,3-diaza-1-yl-2-diazano-1-yloxyl-1-tricarbano-1-oxent hydrochloride 23: nordiareno-1/3-trihydro-1-oxa-2:2-(biyl-1,5-hexa[6]-carban-1-eno-3-oxent-1-yloxcarbant)-7-chlorant-3-oxent-4,6-diylox-carbant 24: nordiareno-1/3-trihydro-2-aza-1-oxant-3-oxent-1-yl-4-areno-1-chlorant-2-ylsulfazantbioxent 25: diareno-2-aza-1-(ylcarbyl-4-areno-1,2-diyloxcarbant)-6,7-diyloxcarbant hydrochloride 26: homodiareno-7-hydro-5,8-diaza-2-chlorant-8-oxent-9-ylarene-6-ylazcarbant 27: tri[2$^{4}$1]areno-2$^{4z}$-homo-1$^{6}$-nor-1,2$^{3/4z}$-octahydro-1$^{3}$,2$^{3}$-diaza-1$^{1}$-oxa-3$^{1}$-chlorant-2$^{4}$-oxent-1$^{2}$-yl-2-areno-1-chlorant 28: tri[3]areno-2$^{1,4}$-dihydro-2$^{1}$-aza-2$^{4}$-sulfa-1$^{6}$-chlorant-2$^{1}$-yl-3-tricarbano-1-ylazbicarbant 29: tri[3]areno-2$^{1,4}$-dihydro-2$^{1}$-sulfa-2$^{4}$-(yliden-3-tricarbano-1-yl-4-cyclohexacarbano-1,4-diaza-1-carbant)-1$^{6}$-ylsulf-bioxentylazbicarbant 30: tri[3]areno-2$^{6z}$-homo-2$^{4}$-hydro-2$^{1}$-aza-2$^{4}$-sulfa-1$^{6}$-chlorant-2$^{6z}$-yl-4-cyclohexacarbano-1,4-diaza-1-carbant 31: tri[3]areno-2$^{4}$-nor-1$^{1:5}$-cyclo-1,2$^{1}$,3$^{1}$, 4-nonahydro-1$^{3,6}$-diaza-3$^{2}$-azant-3$^{3}$-carbant-2$^{1}$-(ylcarbyloxylcarbazantoxent)-1$^{2}$-yloxcarbant 32: tetra[4]areno-1$^{1/4}$,2$^{1,2}$3$^{1,4}$-octahydro-3$^{1}$-carbant-1$^{3,6}$,2$^{4}$,-3$^{1}$,4$^{4}$-pentaoxant-1$^{4}$,3$^{4}$-dioxent-1$^{1}$-(ylazbicarbant)-1$^{5}$-ylcarb-azantoxent 33: penta[3$^{4}$2]areno-4$^{6}$-nor-2$^{3}$, 4$^{1}$-diaza-1,2,3$^{3,4}$-dodecahydro-1$^{1}$-(ylcarbacidocarbant)-1$^{6}$,5$^{2}$-di(yloxcarbant)-1$^{5}$-yloxylcarb-oxentyl-5-areno-1,2,3-triyloxcarbant 34: tetra[3$^{4}$1]areno-2$^{1}$-nor-2,3,4$^{1,6}$-nonahydro-2$^{4}$,4$^{6}$-diaza-2$^{2:4^6}$-biyl-1,2-dicarbane-3$^{4}$-(o xantylcarbacidocarbant)-2$^{4}$-(ylcarb-oxent)-3$^{2}$-yldicarbane-1$^{5}$-(yloxcarbant)-3$^{3}$-(yloxyl-1-di-carbanooxent)-1$^{6}$-yl-7-dicycloundeca[10.$^{1:5}$1]carbano-1-aza-8(2:3)-(nordiareno-1-(hydroazade))-3-oxant-7-(ylcarbacido-carbant)-3-yldicarbane 35: tetra[3$^{4}$1]areno-2,3,4-dodecahydro-2$^{4}$-oxa-2$^{1}$;3$^{1}$-biyl-1,2-(dicarbanooxade)-1$^{5}$,2$^{3}$,4$^{3,3}$-tetracarbant-1$^{1}$-oxant

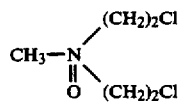
(1)

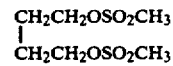
(2)

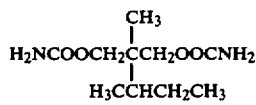
(3)

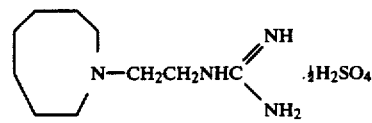
(4)

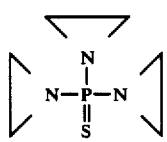
(5)

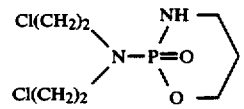
(6)

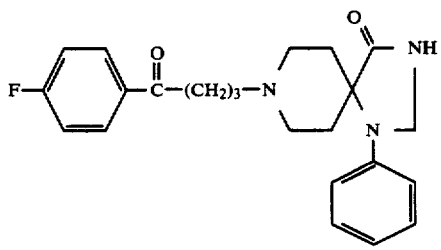
(7)

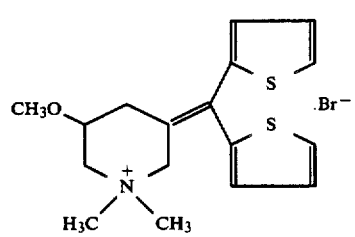
(8)

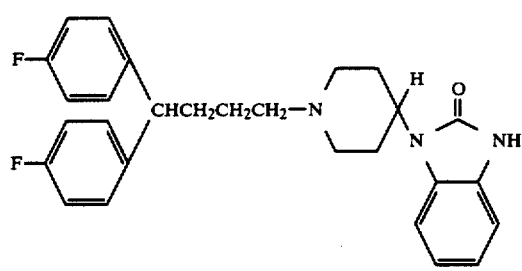 (9)
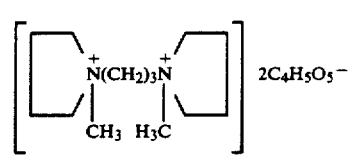 (10)
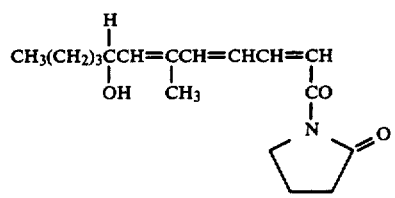 (11)
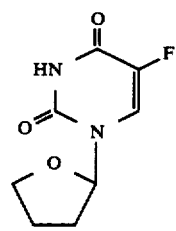 (12)
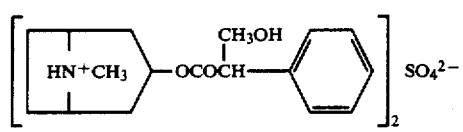 (13)
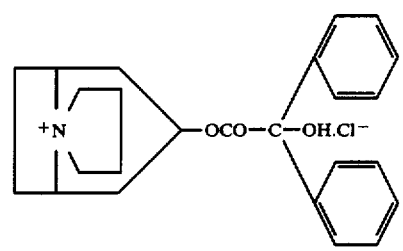 (14)
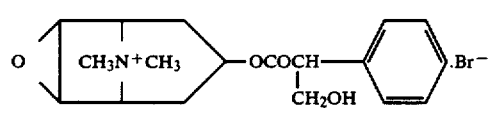 (15)
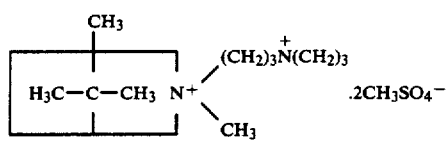 (16)
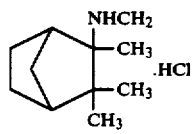 (17)
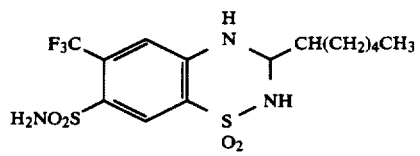 (18)
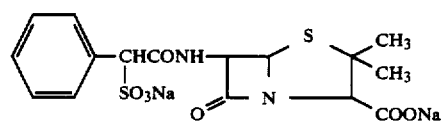 (19)
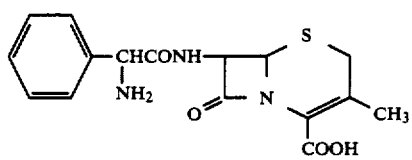 (20)
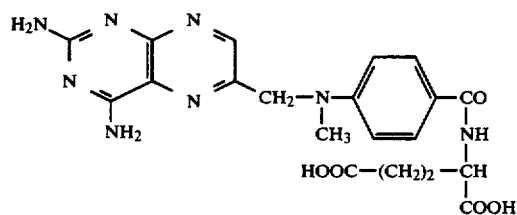 (21)
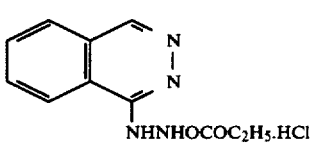 (22)

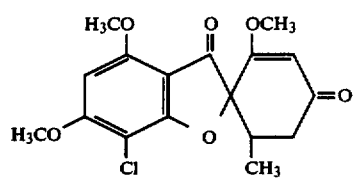 (23)
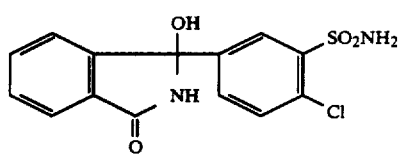 (24)
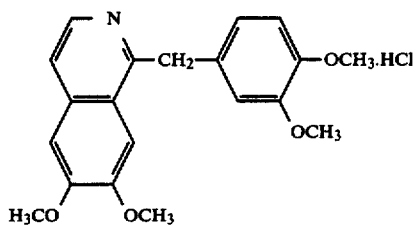 (25)
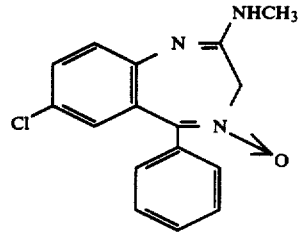 (26)
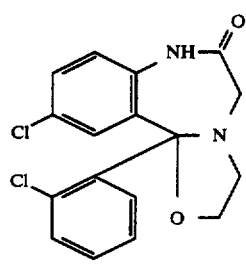 (27)
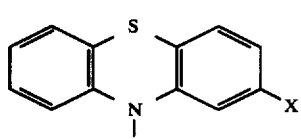 (28)
R = —(CH$_2$)$_3$N(CH$_3$)$_2$
X = —Cl
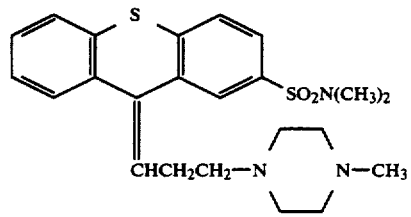 (29)
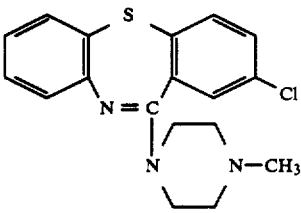 (30)
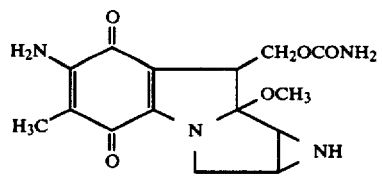 (31)
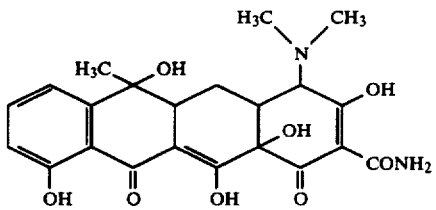 (32)
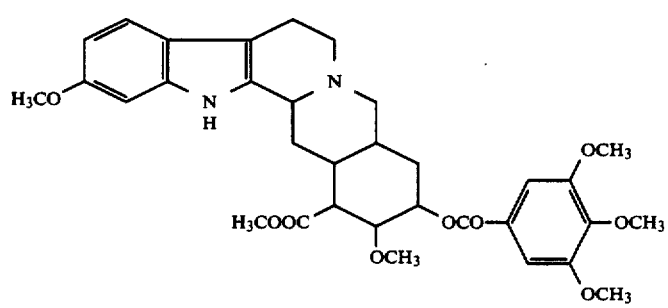 (33)

In order to further facilitate better understanding of the preferred process according to the present invention, a print-out of a computer program according to the present invention has been submitted as an appendix which is retained in the file of this patent. The appended program was written for a "FACOM 9450-II" to run under the APCS operating system and business BASIC.

What is claimed is:

1. A method for naming a chemical compound comprising the steps of:
   presetting name stems and predetermined first, second and third rules in a memory of a data processing device:
   inputting input data representative of a chemical compound to be named into said data processing system through an input means;
   breaking down said input data into a plurality of data components, each of which is representative of an individual constituent element of said compound;
   identifying a first data component of said data components, said first data component constituting the core of said compound according to said predetermined first rules;
   naming said first data component according to said predetermined second rules;
   establishing a connection table on the basis of said first component and storing said connection table in a connection table memory;
   naming a second data component of said data components according to said predetermined third rules;
   modifying said connection table in said connection table memory by adding the name given for said second component to said connection table;
   repeating said steps of naming said second component and modifying said connection table for all of the second components on said compound; and
   determining name of said compound based on said connection table and displaying the determined name.

2. The method as set forth in claim 1, wherein said chemical compound is an organic compound.

3. The method as set forth in claim 2, wherein said first data component is classified from among a first group consisting of acyclic hydrocarbons, a second group consisting of alicyclic hydrocarbon compounds, a third group consisting of aromatics excepting those classified in a fourth group, and said fourth group consisting of cyclic fused aromatic rings, each group having corresponding noncarbon isohydrides.

4. The method as set forth in claim 3, wherein said first data component to be classified in said first and second groups are skeletal atoms.

5. The method as set forth in claim 4, wherein said first data component to be classified in said third and fourth groups are aromatic rings.

6. The method as set forth in claim 4, wherein the original name and numbering of said skeletal atoms used in the nomenclature of the original constitutional element are retained as unique characteristics of the element even when said components are mutually bonded to form a different type of organic compound.

7. The method as set forth in claim 1, wherein all the names given to the chemical compounds begin with the name of said first data component.

8. The method as set forth in claim 7, wherein said names given to said second components follow said name of said first data component.

9. The method as set forth in claim 8, wherein a natural language is used in the formula notation.

10. A system for naming chemical compounds comprising:
    storage means for storing name stems and rules for naming compounds;
    input means for inputting data concerning chemical compounds;
    processing means for accepting data from the input means, retrieving name stems and reles from said storage means manipulating data accepted from said input means according to said rules stored in said storage means said processing means manipulating said input data by identifying a first component constituting the core of said compound according to predetermined first rules, naming said first component according to predetermined second rule, identifying a secondary component according and naming said secondary component of said first component according to a predetermined third rule, modifying the name given for said first component by adding the name given for said secondary component to said name of said first component, and repeating said secondary component naming and name-modifying steps for all of the secondary components in said compound; and outputting means for displaying the results of the manipulation performed by said processing means.

11. The apparatus as set forth in claim 9, wherein said input means is adapted to accept data in the form of the chemical formula of said compound to be named.

12. The apparatus as set forth in claim 10, wherein said output means is associated with said input means for displaying input data.

13. The apparatus as set forth in claim 12, wherein said output means incorporates a graphic display, and said input means allows graphic input.

14. The apparatus as set forth in claim 9, wherein said storage means stores said name stems in the form of a table.

15. The apparatus as set forth in claim 9, wherein said processing means manipulates said input data by:
   identifying a first component constituting the core of said compound according to predetermined first rules;
   naming said first component according to predetermined second rules;
   naming a secondary component of said first component according to predetermined third rules;
   modifying the name given for said first component by adding the name given for said second component to said name of said first component; and
   repeating said secondary-component naming and name-modifying steps for all of the secondary components in said compound.

16. The apparatus as set forth in claim 15, wherein said chemical compound is an organic compound.

17. The apparatus as set forth in claim 16, wherein said first component is classified from among a first group consisting of acyclic hydrocarbons, a second group consisting of alicyclic hydrocarbon compounds, a third group consisting of aromatics excepting those classified in a fourth group, and said fourth group consisting of cyclic fused aromatic rings, each group having corresponding noncarbon isohydrides.

18. The apparatus as set forth in claim 17, wherein said first component to be classified in said first and second groups are skeletal atoms.

19. The apparatus as set forth in claim 18, wherein said first component to be classified in said third and fourth groups are aromatic rings.

20. The apparatus as set forth in claim 18, wherein the original name and numbering of said skeletal atoms used in the nomenclature of the original constitutional element are retained as unique characteristics of the element even when said components are mutually bonded to form a different type of organic compound.

21. The apparatus as set forth in claim 10, wherein all the names given to the chemical compounds begin with the name of said first component.

22. The apparatus as set forth in claim 21, wherein said names given to said second components follow said name of said first component.

23. The apparatus as set forth in claim 22, wherein natural language is used in the formula notation.

24. A digital processor device for naming a chemical compound comprising:

storage means for storing a preset name stem table and a connection table;

inputting means for inputting data concerning the chemical compound to be named;

processing means operable in response to input of data through said inputting means, for breaking down input data into a plurality of data components respectively representative of individual constituent elements of said chemical compound, identifying and naming a first data component among said plurality of data components and constituting the core of the chemical compound, establishing a basic connection table based on the identified first data component, storing said basic connection table in said storage means, updating said connection table based on the identification and naming of each of second data components constituted by the data components other than said first data component in one-by-one basis in a predetermined order; and outputting means for outputting a data representative of the resultant name of said chemical compound.

25. A data processing device for interconversion between the chemical structure and the name of a chemical compound comprising:
   first storage means for storing name stems and rules for naming compounds;
   second storage means storing given name for chemical compound, said second storage means being adapted to be updated the stored data every time a name is given for a new compound;
   inputting means for inputting data concerning chemical compound, said inputting means capable of operating in a first mode for accepting first mode input of the chemical structure of said chemical compound and capable of operating in a second mode for accepting second mode input of the known name of said chemical compound for generating input data including identification of required mode operation;
   a processor means operable in response to input data from said inputting means, for performing first mode processing in response to said first mode input for naming chemical compound based on said input data representative of chemical structure thereof and for performing second mode processing in response to second mode input for reading out known chemical structure corresponding to input data representative of the known name of said chemical compound, said processor means, in said first mode operation, retrieving name stems and rules from said first storage means and processing data accepted from said input means according to said rules stored in said storage means; and
   a display means for displaying resultant of interconversion between chemical structure and name of said chemical compound.

26. A data processing device as set forth in claim 25, wherein said inputting means comprises a text input accepting means for accepting said second mode input and a grahic input means for accepting said first mode input.

* * * * *